United States Patent
Atterbury et al.

(10) Patent No.: US 12,420,018 B2
(45) Date of Patent: Sep. 23, 2025

(54) DEVICES AND PROCESSES FOR DELIVERY OF THERAPEUTIC FLUIDS

(71) Applicant: Eli Lilly and Company, Indianapolis, IN (US)

(72) Inventors: William Godwin Atterbury, Columbus, OH (US); Corrie Jo Bennison, Lewis Center, OH (US); Jeffrey Leclair Ellis, Columbus, OH (US); David Arthur Holley, Lancaster, OH (US); Beverly Ann Piatt, Columbus, OH (US); John Paul Tallarico, Powell, OH (US)

(73) Assignee: Eli Lilly and Company, Indianapolis, IN (US)

( * ) Notice: Subject to any disclaimer, the term of this patent is extended or adjusted under 35 U.S.C. 154(b) by 1147 days.

(21) Appl. No.: 17/299,850

(22) PCT Filed: Dec. 12, 2019

(86) PCT No.: PCT/US2019/065904
§ 371 (c)(1),
(2) Date: Jun. 4, 2021

(87) PCT Pub. No.: WO2020/131552
PCT Pub. Date: Jun. 25, 2020

(65) Prior Publication Data
US 2022/0111147 A1    Apr. 14, 2022

Related U.S. Application Data

(60) Provisional application No. 62/781,662, filed on Dec. 19, 2018.

(51) Int. Cl.
*A61M 5/20* (2006.01)
*A61M 5/32* (2006.01)

(52) U.S. Cl.
CPC ........ *A61M 5/2046* (2013.01); *A61M 5/2033* (2013.01); *A61M 5/3204* (2013.01);
(Continued)

(58) Field of Classification Search
CPC .. A61M 5/2046; A61M 5/2033; A61M 5/155; A61M 2005/2026;
(Continued)

(56) References Cited

U.S. PATENT DOCUMENTS 2,390,246 A   12/1945  Folkman
2,446,429 A    8/1948  Nelson et al.
(Continued)

FOREIGN PATENT DOCUMENTS

DE   3809482   10/1989
EP   2221076    8/2010
(Continued)

OTHER PUBLICATIONS

International Search Report of the International Searching Authority pertaining to International Application No. PCT/US2019/065904; Date of Mailing: Mar. 11, 2020; pp. 6.
(Continued)

*Primary Examiner* — Kevin C Sirmons
*Assistant Examiner* — Leah J Swanson
(74) *Attorney, Agent, or Firm* — Jonathan C. Anderson

(57) ABSTRACT

A therapeutic agent delivery system comprises a housing. A therapeutic agent delivery assembly is carried by the housing. The therapeutic agent delivery assembly comprises a chamber having a passageway. A therapeutic agent is carried in the passageway, and a needle is in communication with the passageway. The therapeutic agent delivery assembly may be translatable relative to the housing from a stowed configuration to a deployed configuration. Actuation of a user input may translate the therapeutic agent delivery
(Continued)

assembly from the stowed configuration to the deployed configuration. An input restraint may be rotatable relative to the housing from a first rotational configuration to a second rotational configuration. In the first rotational configuration the input restraint may inhibit actuation of the user input, and in the second rotational configuration the input restraint may permit actuation of the user input.

17 Claims, 30 Drawing Sheets

(52) U.S. Cl.
CPC ............... *A61M 2005/2026* (2013.01); *A61M 2005/208* (2013.01)

(58) Field of Classification Search
CPC .. A61M 2005/208; A61M 2005/14204; A61M 2205/8218; A61M 2205/8225; A61M 2205/8231; A61M 5/3204; A61M 5/3135; A61M 5/50; A61M 5/20; A61M 5/19; A61M 2005/2013; A61M 2005/206
See application file for complete search history.

(56) References Cited

U.S. PATENT DOCUMENTS

| | | | |
|---|---|---|---|
| 2,833,745 A | 5/1958 | Fikentscher | |
| 2,923,243 A | 2/1960 | Crockford et al. | |
| 3,405,845 A | 10/1968 | Cook et al. | |
| 3,467,526 A | 9/1969 | Mitchell et al. | |
| 3,556,803 A | 1/1971 | Ehrreich, III et al. | |
| 3,594,410 A | 7/1971 | Cohen et al. | |
| 3,754,993 A | 8/1973 | Oguchi et al. | |
| 3,773,111 A | 11/1973 | Dunn | |
| 3,968,796 A | 7/1976 | Baker | |
| 4,031,889 A | 6/1977 | Pike | |
| 4,203,441 A | 5/1980 | Theeuwes | |
| 4,675,174 A | 6/1987 | Eckenhoff | |
| 4,744,786 A | 5/1988 | Hooven | |
| 4,785,972 A | 11/1988 | LeFevre | |
| 4,795,748 A | 1/1989 | Ross et al. | |
| 5,034,114 A | 7/1991 | Kukin | |
| 5,062,834 A | 11/1991 | Gross et al. | |
| 5,151,093 A | 9/1992 | Theeuwes et al. | |
| 5,167,641 A | 12/1992 | Schmitz | |
| 5,304,128 A | 4/1994 | Haber et al. | |
| 5,312,389 A | 5/1994 | Theeuwes et al. | |
| 5,398,850 A | 3/1995 | Sancoff et al. | |
| 5,478,316 A | 12/1995 | Bitdinger et al. | |
| 5,518,145 A | 5/1996 | Chen | |
| 5,540,665 A | 7/1996 | Mercado et al. | |
| 5,645,824 A | 7/1997 | Lim et al. | |
| 5,700,245 A | 12/1997 | Sancoff et al. | |
| 5,855,761 A | 1/1999 | Joshi | |
| 5,858,001 A | 1/1999 | Tsals et al. | |
| 5,871,125 A | 2/1999 | Gross | |
| 5,891,087 A | 4/1999 | Ohtani et al. | |
| 5,941,857 A | 8/1999 | Nguyen et al. | |
| 5,992,700 A | 11/1999 | McGlothlin et al. | |
| 6,086,568 A | 7/2000 | Caizza | |
| 6,086,569 A | 7/2000 | Schweizer | |
| 6,099,504 A * | 8/2000 | Gross ................. | A61M 5/2046 604/145 |
| 6,156,014 A | 12/2000 | Petersen et al. | |
| 6,270,479 B1 | 8/2001 | Bergens et al. | |
| 6,431,468 B1 | 8/2002 | Brown et al. | |
| 6,575,961 B2 | 6/2003 | Joshi | |
| 6,786,365 B2 | 9/2004 | Kim | |
| 6,830,560 B1 | 12/2004 | Gross et al. | |
| 6,913,593 B1 | 7/2005 | Alexandre et al. | |
| 6,964,356 B2 | 11/2005 | Kim | |
| 7,632,245 B1 | 12/2009 | Cowan et al. | |
| 7,717,877 B2 | 5/2010 | Lavi et al. | |
| 7,753,884 B2 | 7/2010 | Gallnböck | |
| 7,985,309 B2 | 7/2011 | Kim | |
| 7,988,663 B2 | 8/2011 | Schiller et al. | |
| 8,157,769 B2 | 4/2012 | Cabiri | |
| 8,353,426 B2 | 1/2013 | Wold et al. | |
| 8,353,679 B2 | 1/2013 | Yamamoto et al. | |
| 9,233,209 B2 | 1/2016 | Markussen et al. | |
| 9,321,581 B2 | 4/2016 | Bennison et al. | |
| 9,402,957 B2 | 8/2016 | Adams et al. | |
| 9,795,740 B2 | 10/2017 | Heintz et al. | |
| 2001/0025168 A1 | 9/2001 | Gross et al. | |
| 2001/0050085 A1 | 12/2001 | Knudson et al. | |
| 2002/0156461 A1 | 10/2002 | Joshi | |
| 2003/0168480 A1 | 9/2003 | Kim | |
| 2004/0249339 A1 | 12/2004 | Willis et al. | |
| 2005/0006401 A1 | 1/2005 | Kim | |
| 2005/0063766 A1 | 3/2005 | Chen et al. | |
| 2005/0187522 A1 | 8/2005 | Miller | |
| 2006/0235264 A1 | 10/2006 | Vassallo | |
| 2007/0088268 A1 | 4/2007 | Edwards | |
| 2007/0088337 A1 | 4/2007 | Lautenbach | |
| 2007/0173770 A1 | 7/2007 | Stamp | |
| 2007/0228071 A1 | 10/2007 | Kamen et al. | |
| 2007/0233001 A1 | 10/2007 | Burroughs et al. | |
| 2008/0066766 A1 | 3/2008 | Paraschac et al. | |
| 2008/0147006 A1 | 6/2008 | Brunnberg et al. | |
| 2008/0233029 A1 | 9/2008 | Fan et al. | |
| 2008/0257915 A1 | 10/2008 | Wold | |
| 2008/0262427 A1 | 10/2008 | Hommann | |
| 2009/0093787 A1 | 4/2009 | Barbour | |
| 2009/0131860 A1 | 5/2009 | Nielsen | |
| 2009/0227942 A1 | 9/2009 | Stroem Hansen et al. | |
| 2009/0259176 A1 | 10/2009 | Yairi | |
| 2009/0259179 A1 | 10/2009 | Hillios et al. | |
| 2009/0292246 A1 | 11/2009 | Slate et al. | |
| 2010/0030152 A1 | 2/2010 | Lee et al. | |
| 2010/0063444 A1 | 3/2010 | Wikner | |
| 2010/0069846 A1 | 3/2010 | Stamp | |
| 2010/0137808 A1 | 6/2010 | Wilmot et al. | |
| 2010/0152660 A1 | 6/2010 | Mack et al. | |
| 2010/0174225 A1 | 7/2010 | Pesach et al. | |
| 2010/0292653 A1 | 11/2010 | Maritan | |
| 2011/0054390 A1 | 3/2011 | Searle et al. | |
| 2011/0092906 A1 | 4/2011 | Bottger et al. | |
| 2011/0270188 A1 | 11/2011 | Caffey et al. | |
| 2011/0272271 A1 | 11/2011 | Hong et al. | |
| 2012/0078216 A1 | 3/2012 | Smith et al. | |
| 2012/0130313 A1 | 5/2012 | Byerly et al. | |
| 2013/0253472 A1 | 9/2013 | Cabiri | |
| 2013/0274676 A1 * | 10/2013 | Ekman ............. | A61M 5/31513 604/197 |
| 2013/0324934 A1 | 12/2013 | Holmqvist et al. | |
| 2014/0012229 A1 | 1/2014 | Bokelman et al. | |
| 2014/0103075 A1 | 4/2014 | Bennison et al. | |
| 2014/0180218 A1 | 6/2014 | Fourt et al. | |
| 2014/0257193 A1 | 9/2014 | Boström et al. | |
| 2014/0309591 A1 | 10/2014 | Holmqvist | |
| 2014/0330216 A1 | 11/2014 | Weaver et al. | |
| 2015/0045729 A1 | 2/2015 | Denzer et al. | |
| 2015/0157790 A1 | 6/2015 | Henderson et al. | |
| 2015/0314070 A1 * | 11/2015 | Heintz ................. | C06D 5/10 60/407 |
| 2015/0363097 A1 | 12/2015 | Draper et al. | |
| 2016/0156060 A1 | 6/2016 | Hamelers et al. | |
| 2016/0213846 A1 | 7/2016 | Bennison et al. | |
| 2016/0213847 A1 | 7/2016 | Bennison et al. | |
| 2016/0213859 A1 | 7/2016 | Sadowski et al. | |
| 2017/0014575 A1 | 1/2017 | Hansen et al. | |
| 2017/0098058 A1 | 4/2017 | McCullough et al. | |
| 2017/0224926 A1 | 8/2017 | Dennis, Jr. et al. | |
| 2017/0281877 A1 | 10/2017 | Marlin et al. | |
| 2017/0354779 A1 | 12/2017 | Atterbury et al. | |
| 2018/0110926 A1 | 4/2018 | Schrul et al. | |

FOREIGN PATENT DOCUMENTS

| | | |
|---|---|---|
| EP | 2489387 | 8/2012 |
| JP | H03178671 | 8/1991 |
| WO | 92019571 | 11/1992 |

(56) References Cited

FOREIGN PATENT DOCUMENTS

| WO | 95001198 | 1/1995 |
|----|----------|--------|
| WO | 95023641 | 9/1995 |
| WO | 97028750 | 8/1997 |
| WO | 99012593 | 3/1999 |
| WO | 99022790 | 5/1999 |
| WO | 99062576 | 12/1999 |
| WO | 01000270 | 1/2001 |
| WO | 07071485 | 6/2007 |
| WO | 2009040602 | 4/2009 |
| WO | 2009040672 | 4/2009 |
| WO | 09116045 | 9/2009 |
| WO | 09144726 | 12/2009 |
| WO | 2011039212 | 4/2011 |
| WO | 2011075099 | 6/2011 |
| WO | 2012122643 | 9/2012 |
| WO | 2013065055 | 5/2013 |
| WO | 14059444 | 4/2014 |
| WO | 2015160600 | 10/2015 |
| WO | 2016033507 | 3/2016 |
| WO | 2018152018 | 8/2018 |

OTHER PUBLICATIONS

Written Opinion of the International Searching Authority pertaining to International Application No. PCT/US2019/065904; Date of Mailing: Mar. 11, 2020; pp. 12.

"Development of an On-Demand, Generic, Drug-Delivery System," Southern Research Institute, 2000 Ninth Avenue South, Birmingham, AL 35255-5305 Aug. 6, 1985; 30 pages.

Good, Brian T., et al., "An Effervescent Reaction Micropump for Portable Microfluidic Systems," *Lab Chip,* 2006, 6, 659-66; 8 pages.

\* cited by examiner

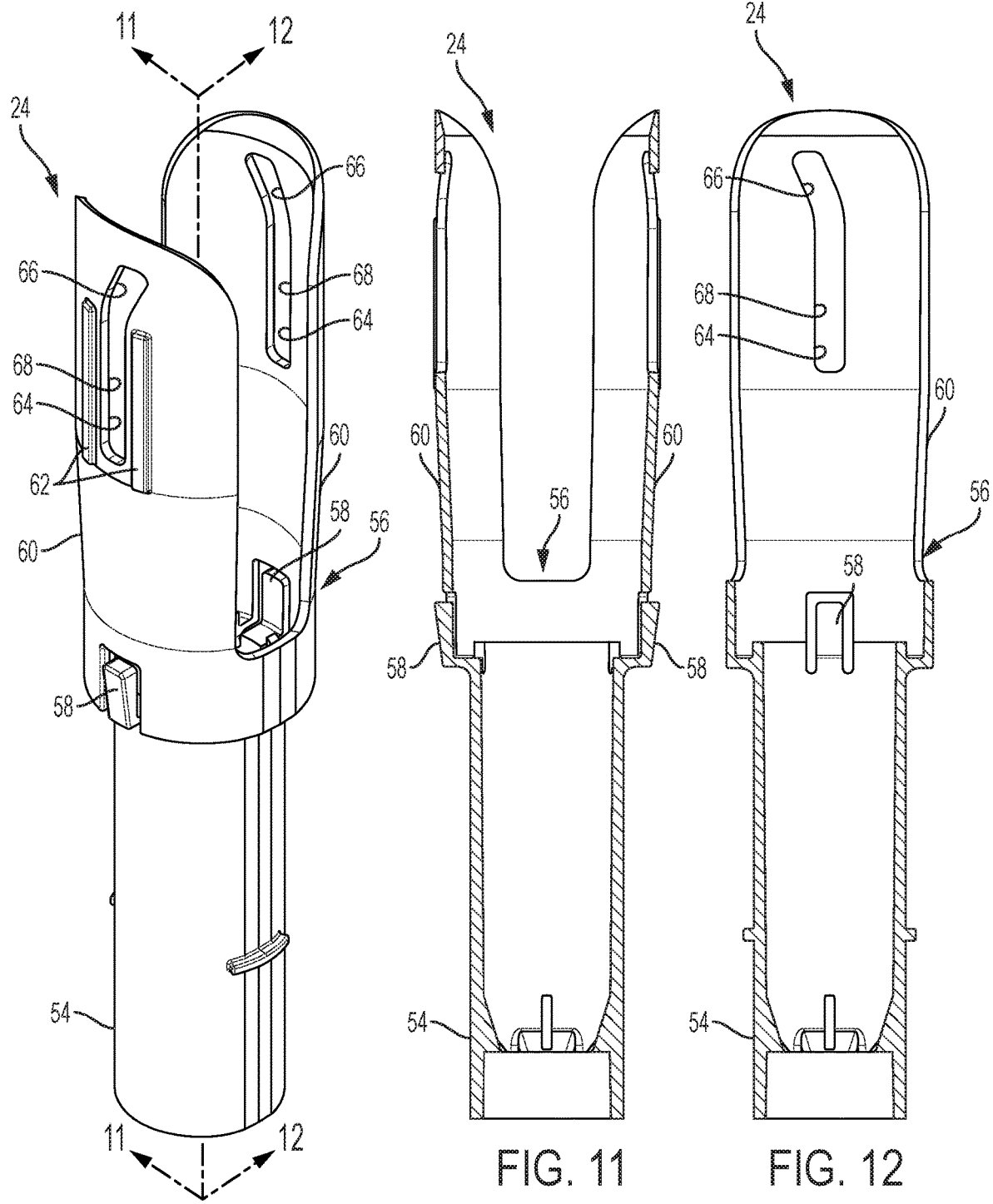

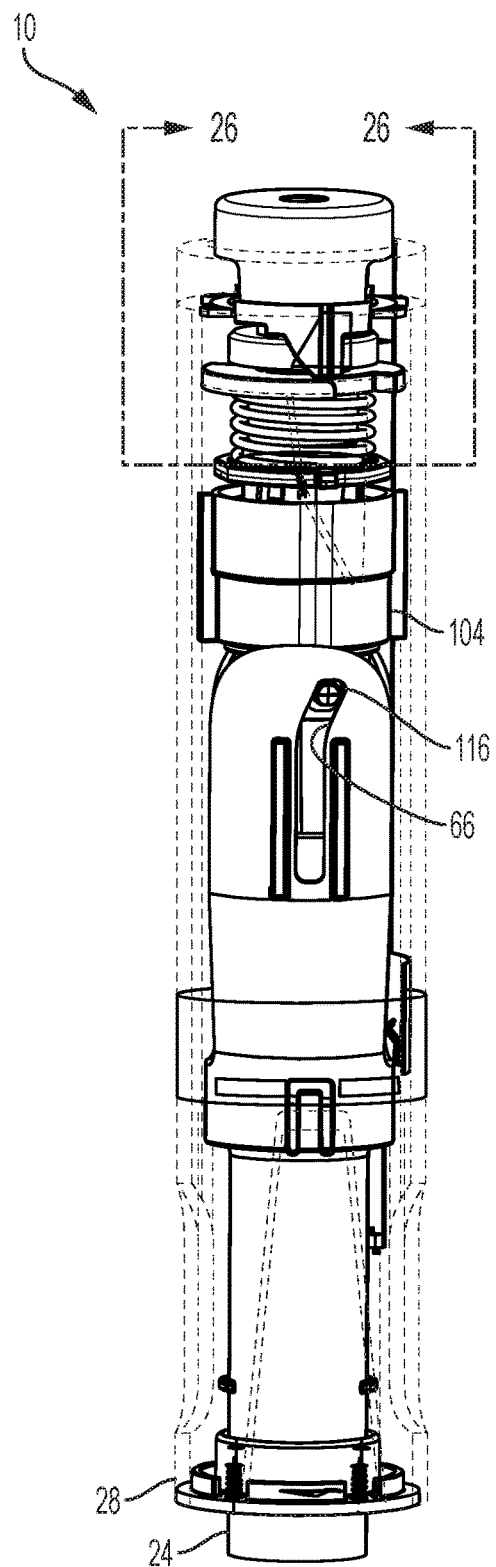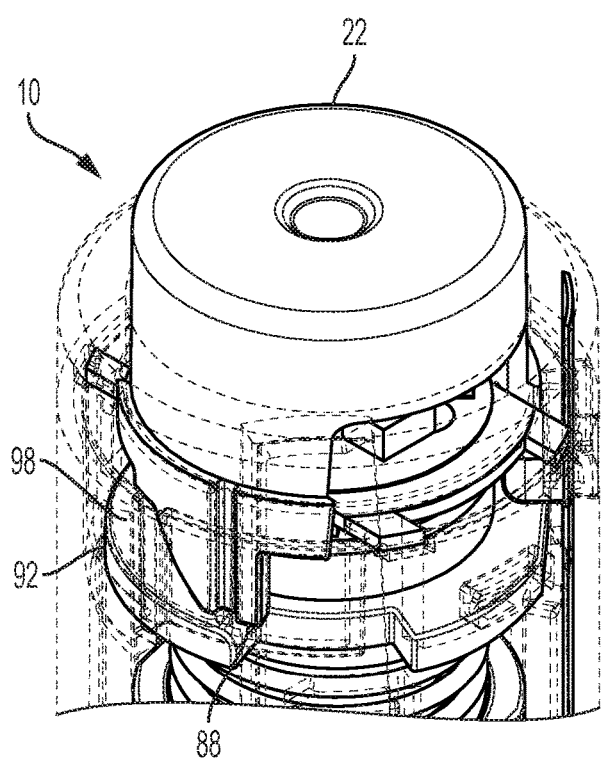
FIG. 25
FIG. 26

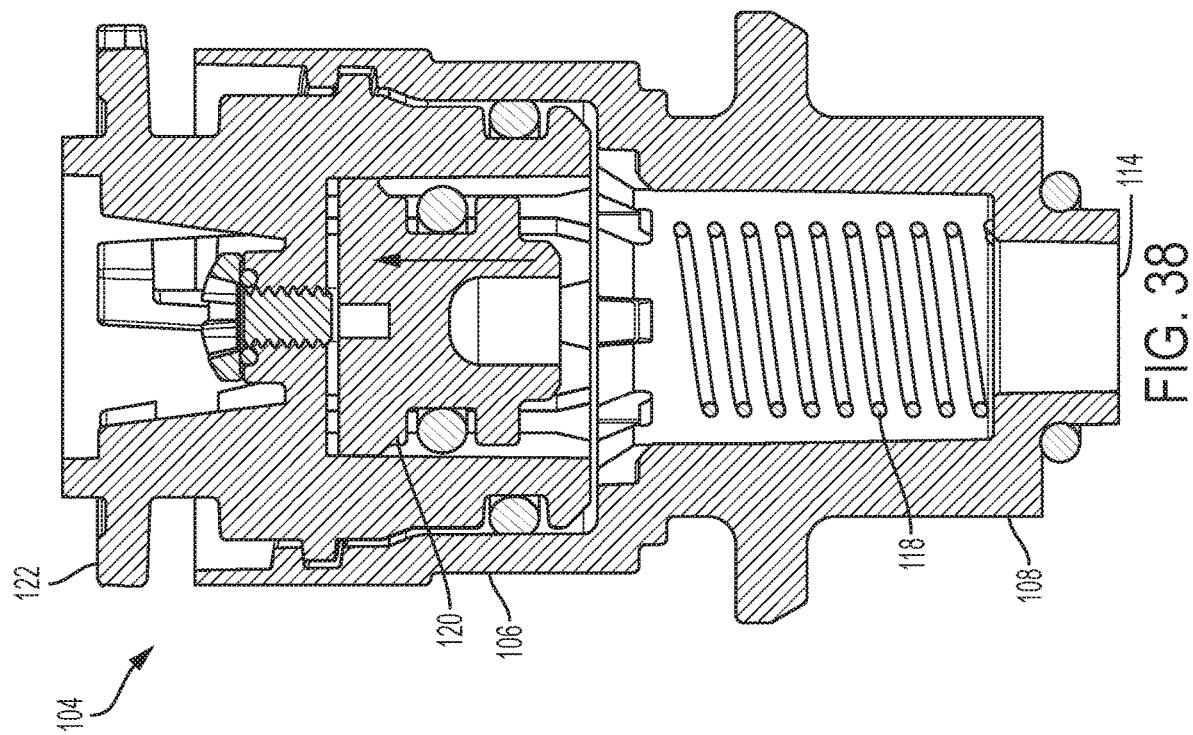
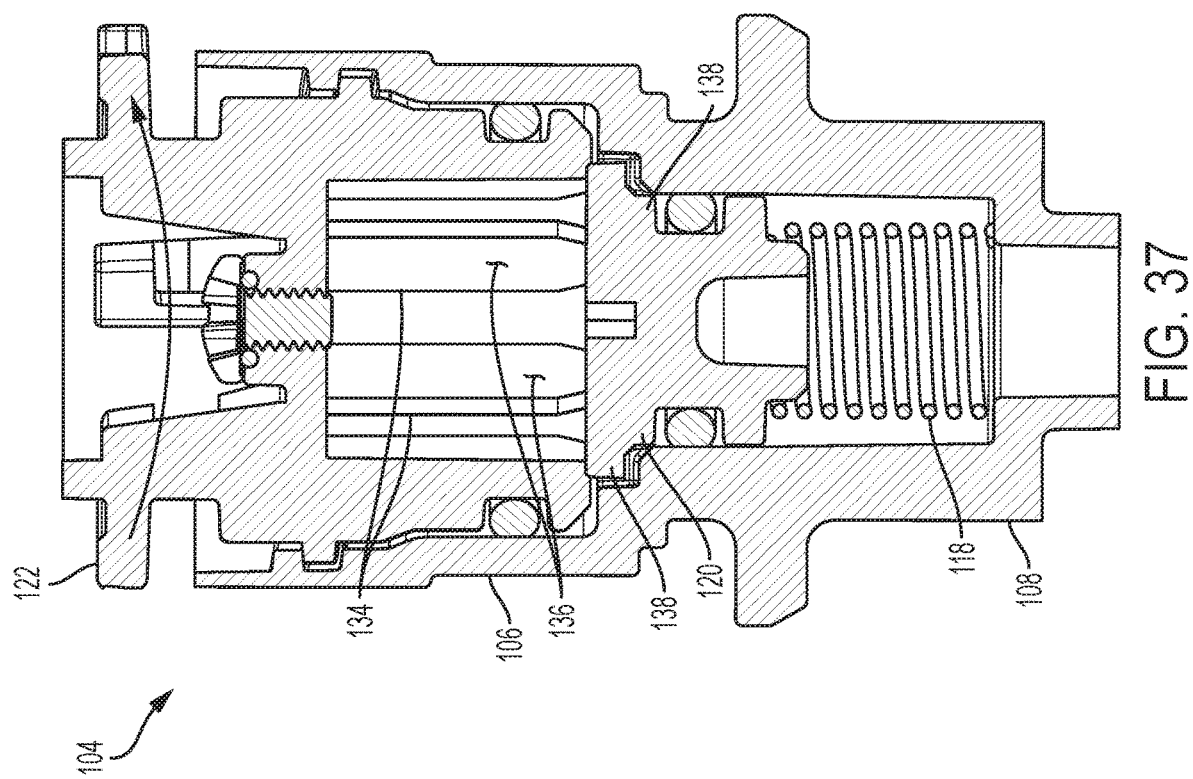

DEVICES AND PROCESSES FOR DELIVERY OF THERAPEUTIC FLUIDS

CROSS-REFERENCE TO RELATED APPLICATIONS

This application is a National Stage of International Application No. PCT/US2019/065904, filed Dec. 12, 2019, which claims priority to U.S. Provisional Application No. 62/781,662, filed Dec. 19, 2018, the disclosures of which are hereby expressly incorporated by reference herein in their entirety.

FIELD OF THE DISCLOSURE

The present disclosure relates to processes and devices for parenteral delivery of therapeutic agents. More particularly, the present disclosure relates to processes and devices for parenteral delivery of high-viscosity therapeutic fluids (for example, protein therapeutics).

BACKGROUND OF THE DISCLOSURE

Protein therapeutics is an emerging class of drug therapy that provides treatment for a broad range of diseases, such as autoimmune disorders, cardiovascular diseases, diabetes, and cancer. A common delivery method for some protein therapeutics, such as monoclonal antibodies, is through intravenous infusion, in which large volumes of dilute solutions are delivered over time. Intravenous infusion usually requires the supervision of a doctor or nurse and is performed in a clinical setting. This can be inconvenient for a patient, and so efforts are being made to permit the delivery of protein therapeutics at home. Desirably, a protein therapeutic formulation can be administered using a syringe for subcutaneous delivery instead of requiring intravenous administration. Subcutaneous injections are commonly administered by laypersons, for example in the administration of insulin by diabetics.

Transitioning therapeutic protein formulations from intravenous delivery to injection devices like syringes and injection pens requires addressing challenges associated with delivering high concentrations of high molecular weight molecules in a manner that is easy, reliable, and causes minimal pain to the patient. In this regard, while intravenous bags typically have a volume of 1 liter, the standard volume for a syringe ranges from 0.3 milliliters up to 25 milliliters. Thus, depending on the drug, to deliver the same amount of therapeutic proteins, the concentration may have to increase by a factor of 40 or more. Also, injection therapy is moving towards smaller needle diameters and faster delivery times for purposes of patient comfort and compliance.

Delivery of protein therapeutics is also challenging because of the high viscosity associated with such therapeutic formulations, and the high forces needed to push such formulations through a parenteral device. Formulations with absolute viscosities above 40-60 centipoise (cP) may be difficult to deliver by conventional spring driven auto-injectors for multiple reasons. Structurally, the footprint of a spring for the amount of pressure delivered is relatively large and fixed to specific shapes, which reduces flexibility of design for delivery devices. Next, auto-injectors are usually made of plastic parts. However, a large amount of energy must be stored in the spring to reliably deliver high-viscosity fluids. If not properly designed, this stored energy may cause damage to the plastic parts due to creep, which is the tendency of the plastic part to permanently deform under stress. An auto-injector typically operates by using the spring to push a needle-containing internal component towards an outer edge of the housing of the syringe. The sound associated with the operation of a spring-based auto-injector may cause patient anxiety, potentially reducing future compliance. The generated pressure versus time profile of such a spring driven auto-injector cannot be readily modified, which prevents users from fine tuning pressure to meet their delivery needs.

It would be desirable to provide processes and devices by which a therapeutic fluid, in particular a high-viscosity fluid, could be self-administered in a reasonable time and with a limited injection space. These processes and devices could be used to deliver high-concentration protein, high-viscosity pharmaceutical formulations, or other therapeutic fluids.

SUMMARY

According to an embodiment of the present disclosure, a therapeutic agent delivery system includes a housing having a distal end portion. A therapeutic agent delivery assembly is carried by the housing. The therapeutic agent delivery assembly includes a chamber having a passageway. A therapeutic agent is carried in the passageway, and a needle is in communication with the passageway. The therapeutic agent delivery assembly is translatable relative to the housing from a stowed configuration to a deployed configuration. In the deployed configuration the needle at least partially extends distally from the distal end portion of the housing. A user input is configured to be actuated by a user. Actuation of the user input translates the therapeutic agent delivery assembly from the stowed configuration to the deployed configuration. An input restraint is rotatable relative to the housing from a first rotational configuration to a second rotational configuration. In the first rotational configuration the input restraint inhibits actuation of the user input, and in the second rotational configuration the input restraint permits actuation of the user input. A sleeve is translatable relative to the housing from an exposed configuration to a retracted configuration. In the exposed configuration the sleeve partially extends distally from the distal end of the housing. The sleeve rotates the input restraint from the first rotational configuration to the second rotational configuration when translating from the exposed configuration to the retracted configuration.

According to another embodiment of the present disclosure, a therapeutic agent delivery system includes a housing having a distal end portion. A therapeutic agent delivery assembly is carried by the housing. The therapeutic agent delivery assembly includes a chamber including a passageway. A therapeutic agent is carried in the passageway. A needle is in communication with the passageway. A pressure generating actuator is in communication with the passageway, and actuation of the pressure generating actuator causes delivery of the therapeutic agent from the passageway to the needle and discharge of the therapeutic agent from the needle. The therapeutic agent delivery assembly is translatable relative to the housing from a stowed configuration to a deployed configuration. In the deployed configuration the needle at least partially extends distally from the distal end portion of the housing. A user input is configured to be actuated by a user. Actuation of the user input actuates the pressure generating actuator. An input restraint is rotatable relative to the housing from a first rotational configuration to a second rotational configuration. In the first rotational configuration the input restraint inhibits actuation of the user input, and in the second rotational configuration the input restraint permits actuation of the user input. A sleeve is translatable relative to the housing from an exposed configuration to a retracted configuration. In the exposed configuration the sleeve partially extends distally from the distal end portion of the housing, and the sleeve rotates the input restraint from the first rotational configuration to the second rotational configuration when translating from the exposed configuration to the retracted configuration.

According to yet another embodiment of the present disclosure, a therapeutic agent delivery system includes a housing having a distal end portion. A therapeutic agent delivery assembly is carried by the housing. The therapeutic agent delivery assembly includes a chamber having a passageway. A therapeutic agent is carried in the passageway. A needle is in communication with the passageway. A pressure generating actuator is in communication with the passageway. Actuation of the pressure generating actuator causes delivery of the therapeutic agent from the passageway to the needle and discharge of the therapeutic agent from the needle. The therapeutic agent delivery assembly is translatable relative to the housing from a stowed configuration to a deployed configuration. In the deployed configuration the needle at least partially extends distally from the distal end portion of the housing. A user input is configured to be actuated by a user. Actuation of the user input translates the therapeutic agent delivery assembly from the stowed configuration to the deployed configuration and actuates the pressure generating actuator. An input restraint is movable relative to the housing from a first configuration to a second configuration. In the first configuration the input restraint inhibits actuation of the user input, and in the second configuration the input restraint permits actuation of the user input. A sleeve is translatable relative to the housing from an exposed configuration to a retracted configuration. In the exposed configuration the sleeve partially extends distally from the distal end portion of the housing, and the sleeve moves the input restraint from the first configuration to the second configuration when translating from the exposed configuration to the retracted configuration.

According to yet another embodiment of the present disclosure, a therapeutic agent delivery system includes a housing having a proximal end portion and a distal end portion. A user input is coupled to the proximal end portion of the housing and is configured to be actuated by a user. A sleeve is coupled to the distal end portion of the housing. A therapeutic agent delivery assembly is carried by the housing. The therapeutic agent delivery assembly includes a chamber including a passageway; a therapeutic agent carried in the passageway; a needle in communication with the passageway; and a pressure generating actuator in communication with the passageway. The therapeutic agent delivery system has a locked configuration in which the sleeve at least partially extends distally from the distal end portion of the housing; an unlocked configuration in which the sleeve is forced into the distal end portion of the housing; a deployed configuration in which the needle at least partially extends distally from the distal end portion of the housing; and an actuated configuration in which a pressurized fluid from the pressure generating actuator causes delivery of the therapeutic agent from the passageway to the needle and discharge of the therapeutic agent from the needle.

BRIEF DESCRIPTION OF THE DRAWINGS

The above-mentioned and other features and advantages of this disclosure, and the manner of attaining them, will become more apparent and will be better understood by reference to the following description of embodiments of the invention taken in conjunction with the accompanying drawings, wherein:

FIG. 10 is a top perspective view of a sleeve of the therapeutic agent delivery system of FIG. 1.

FIG. 11 is a longitudinal sectional view of the sleeve along line 11-11 of FIG. 10.

FIG. 12 is a longitudinal sectional view of the sleeve along line 12-12 of FIG. 10.

FIG. 25 is a side perspective view of the therapeutic agent delivery system of FIG. 1 in a first configuration; the housing is shown in hidden lines to illustrate internal components.

FIG. 26 is a detail top perspective view of the therapeutic agent delivery system within line 26-26 of FIG. 25 and in the first configuration.

FIG. 37 is a longitudinal sectional view of a shuttle of the pressure generating actuator being rotated relative to first and second mixing chambers of the pressure generating actuator and thereby actuating the actuator.

FIG. 38 is a longitudinal sectional view of the shuttle and a mixing piston of the pressure generating actuator in an actuated configuration.

Corresponding reference characters indicate corresponding parts throughout the several views. The exemplifications set out herein illustrate exemplary embodiments of the invention and such exemplifications are not to be construed as limiting the scope of the invention in any manner.

DETAILED DESCRIPTION

The present disclosure relates to systems, devices, and processes for parenteral delivery of therapeutic agents, such as high-viscosity therapeutic fluids.

1. Drugs/Therapeutic Agents

Systems and devices according to the present disclosure may carry and facilitate delivery of a drug to a subject. The term "drug" refers to one or more therapeutic agents including but not limited to insulins, insulin analogs such as insulin lispro or insulin glargine, insulin derivatives, GLP-1 receptor agonists such as dulaglutide or liraglutide, glucagon, glucagon analogs, glucagon derivatives, gastric inhibitory polypeptide (GIP), GIP analogs, GIP derivatives, oxyntomodulin analogs, oxyntomodulin derivatives, therapeutic antibodies and any therapeutic agent that is capable of delivery by devices according to the present disclosure. The drug may be formulated with one or more excipients. Devices according to the present disclosure are operated in a manner generally as described herein by a patient, caregiver or healthcare professional to deliver a drug to a subject.

In certain embodiments, a therapeutic agent is protein, such as a monoclonal antibody or some other protein which is therapeutically useful. In some embodiments, the protein may have a concentration of from about 75 mg/mL to about 500 mg/mL in a fluid. In certain embodiments, the protein may have a concentration of about 150 mg/mL, 200 mg/mL, 250 mg/mL, or more. A drug may further contain a solvent or non-solvent, such as water, perfluoroalkane solvent, safflower oil, or benzyl benzoate.

A drug may be a fluid, more specifically a high-viscosity fluid and may have an absolute viscosity of from about 5 cP to about 1000 cP. In certain embodiments, a high-viscosity fluid has an absolute viscosity of at least about 10 cP, 20 cP, 30 cP, 40 cP, 50 cP, 60 cP, or more.

2. Therapeutic Agent Delivery System

Figure 1:
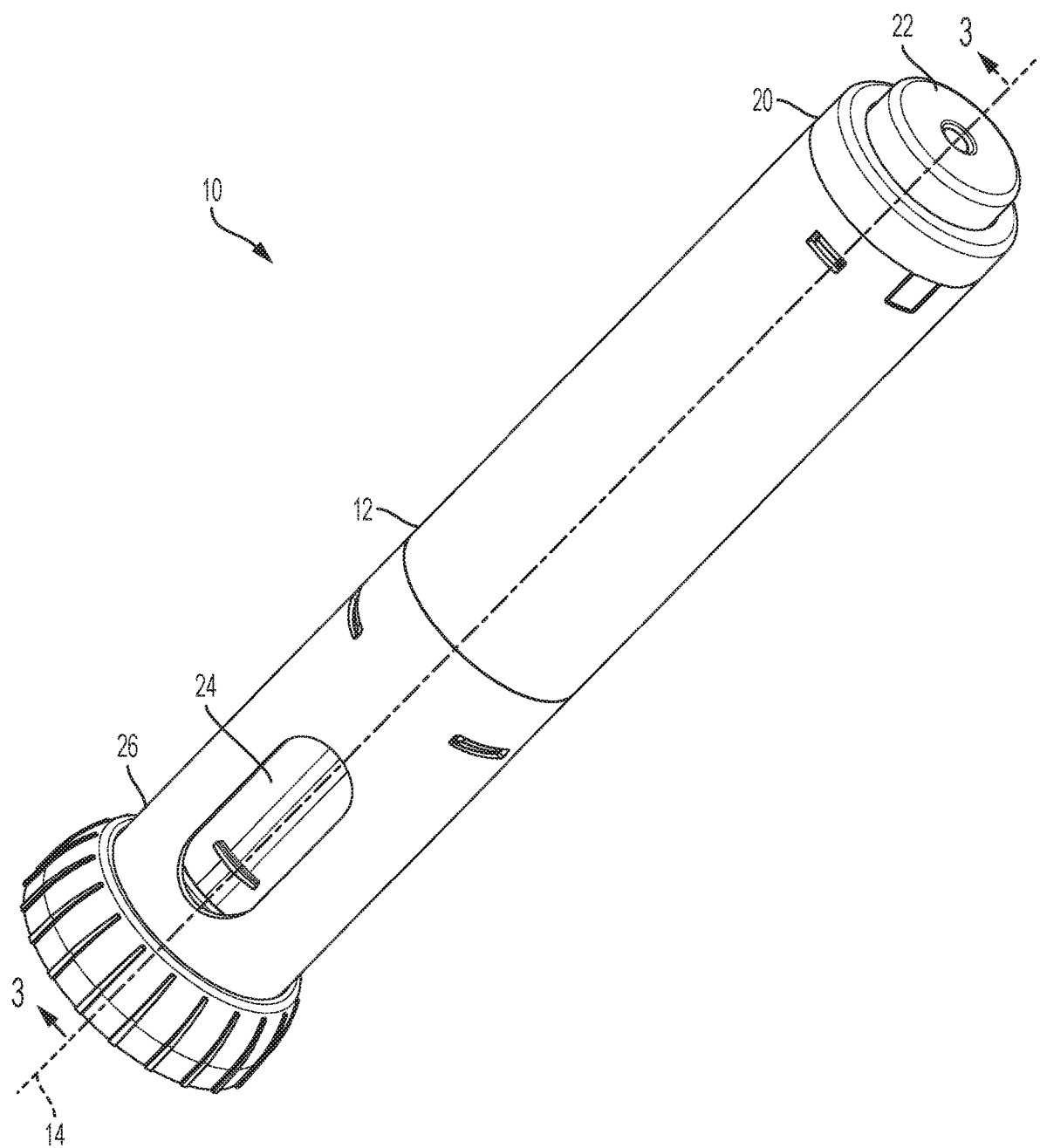
FIG. 1 is a top perspective view of a therapeutic agent delivery system according to an embodiment of the present disclosure.
Figure 2:
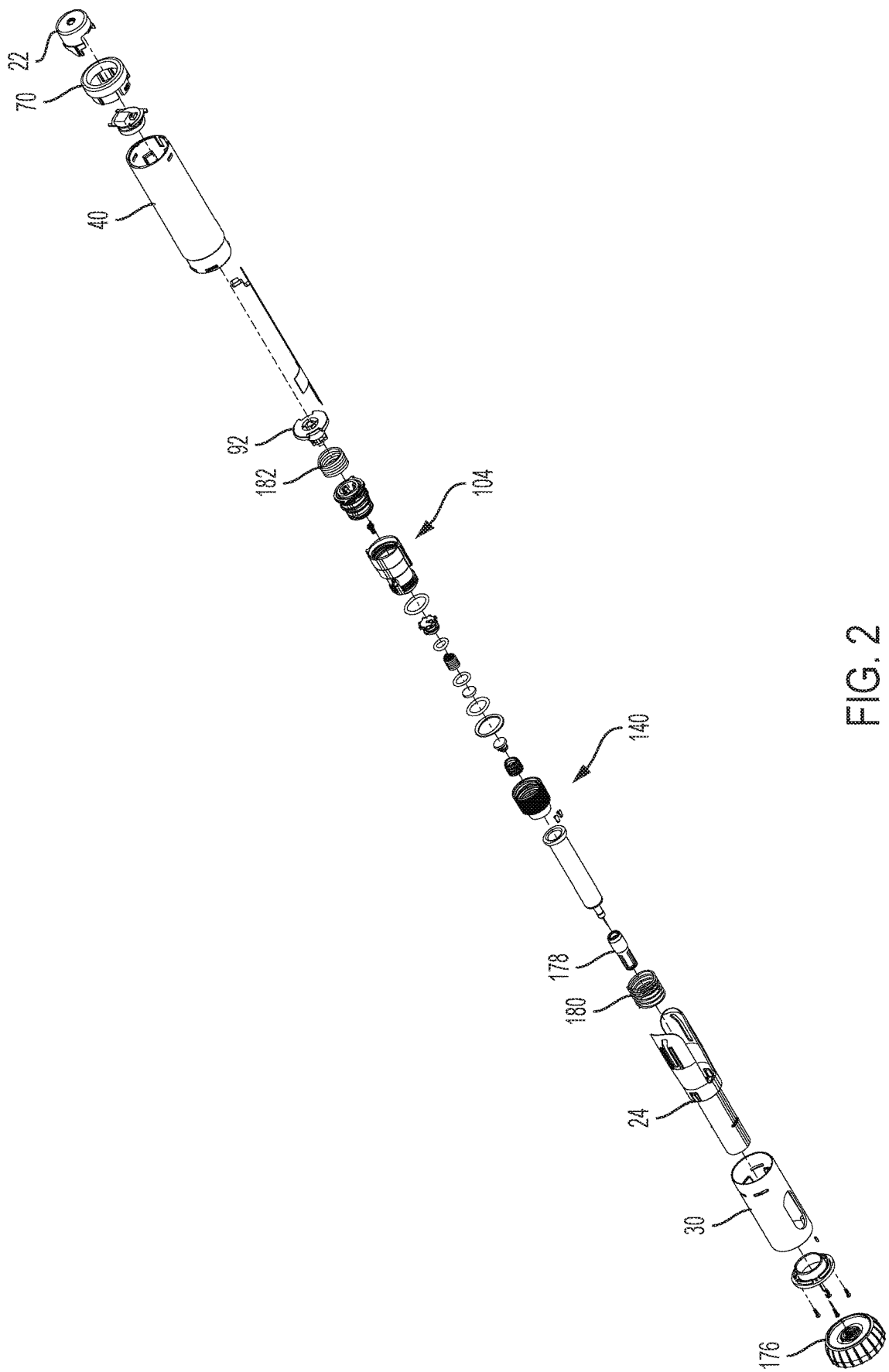
FIG. 2 is an exploded view of the therapeutic agent delivery system of FIG. 1.
Figure 3:
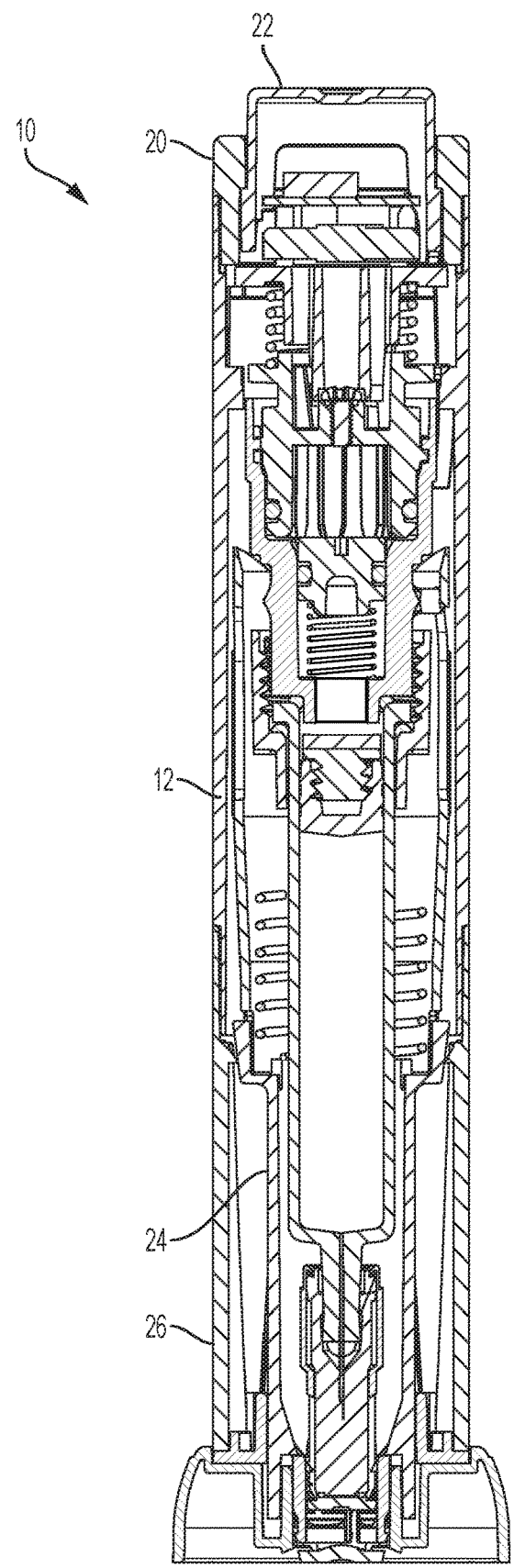
FIG. 3 is a longitudinal sectional view of the therapeutic agent delivery system along line 3-3 of FIG. 1.

FIGS. 1-3 illustrate a therapeutic agent delivery system 10 according to an embodiment of the present disclosure. Illustratively, the therapeutic agent delivery system 10 generally includes the profile of an auto-injector pen, although other profiles may alternatively be used. Generally, the therapeutic agent delivery system 10 includes a housing 12 that is elongated along a longitudinal axis 14. The housing 12 carries a therapeutic agent delivery assembly 16. The therapeutic agent delivery assembly 16 includes a therapeutic agent and a needle 18, and the therapeutic agent delivery assembly 16 translates relative to the housing 12 from a stowed configuration (as illustratively shown in FIGS. 1-3, a configuration in which the needle 18 is disposed entirely within the housing 12) to a deployed configuration (shown elsewhere—for example, a configuration in which the needle 18 is at least partially exposed from the housing 12 and configured to engage the subject and deliver the therapeutic agent to the subject). The therapeutic agent delivery assembly 16 also translates relative to the housing 12 from the deployed configuration to a withdrawn configuration (shown elsewhere—for example, a configuration in which the needle 18 is disposed entirely within the therapeutic agent delivery system 10). A proximal end portion 20 of the therapeutic agent delivery system 10 includes a user input 22 (illustratively, a depressible button) that is actuated to actuate the therapeutic agent delivery assembly 16 (that is, move the needle 18 from the stowed configuration to the deployed configuration and deliver the therapeutic agent to the user). The therapeutic agent delivery system 10 normally inhibits the user input 22 from being actuated (stated another way, the user input 22 is normally "locked"). The therapeutic agent delivery system 10 further includes a sleeve 24 that is normally exposed at a distal end portion 26 of the system 10. The sleeve 24 is pressed against a surface (for example, the skin of a subject) to permit the user input 22 to be actuated (stated another way, to "unlock" the user input 22). The therapeutic agent delivery system 10 may then be actuated by pressing the user input 22. After disengaging the therapeutic agent delivery system 10 from the surface, the needle 18 is translated to the withdrawn configuration and inhibited from being translated to the deployed configuration (stated another way, the system 10 is "locked out"). These aspects, features, and components of the therapeutic agent delivery system 10 are described in further detail below.

Figure 6:
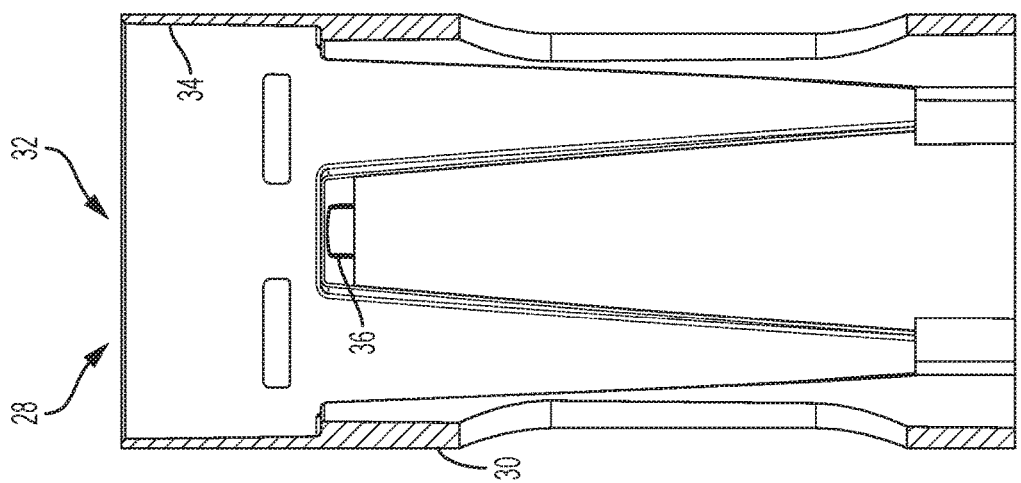
FIG. 6 is a longitudinal sectional view of the distal housing portion along line 6-6 of FIG. 4.
Figure 5:
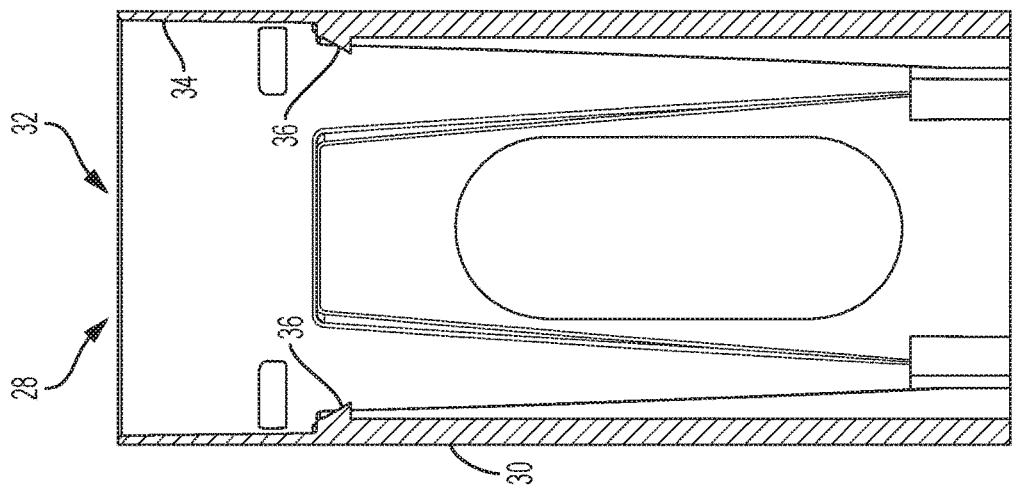
FIG. 5 is a longitudinal sectional view of the distal housing portion along line 5-5 of FIG. 4.
Figure 4:
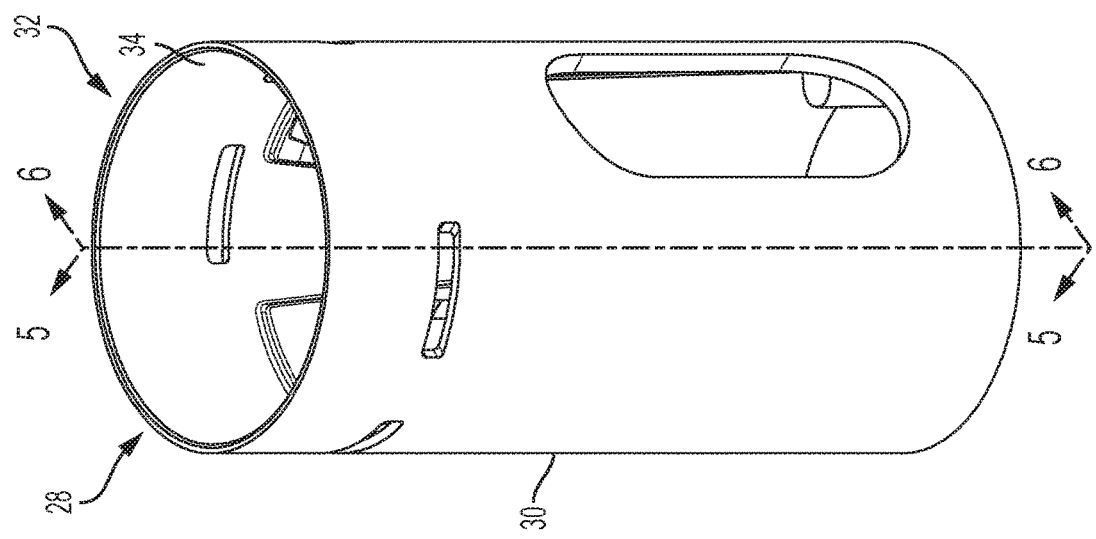
FIG. 4 is a top perspective view of a distal housing portion of a housing of the therapeutic agent delivery system of FIG. 1.

FIGS. 4-6 illustrate a distal housing portion 28 of the housing 12. The distal housing portion 28 includes a main body 30 that has a generally cylindrical shape. The main body 30 includes an inner passageway 32 that carries other components of the therapeutic agent delivery system 10. Adjacent to the inner passageway 32, an inner surface 34 of the distal housing portion 28 carries a restraint feature that, as described in further detail below, selectively engages the therapeutic agent delivery assembly 16. Illustratively, the restraint feature includes two radially-inwardly extending tabs 36. As shown in FIG. 5, the tabs 36 taper radially-inwardly proceeding toward the distal end portion 26 (FIG. 1). In other embodiments, different arrangements of the distal housing portion 28 are possible. For example, the restraint features may be non-tapering tabs.

Figure 7:
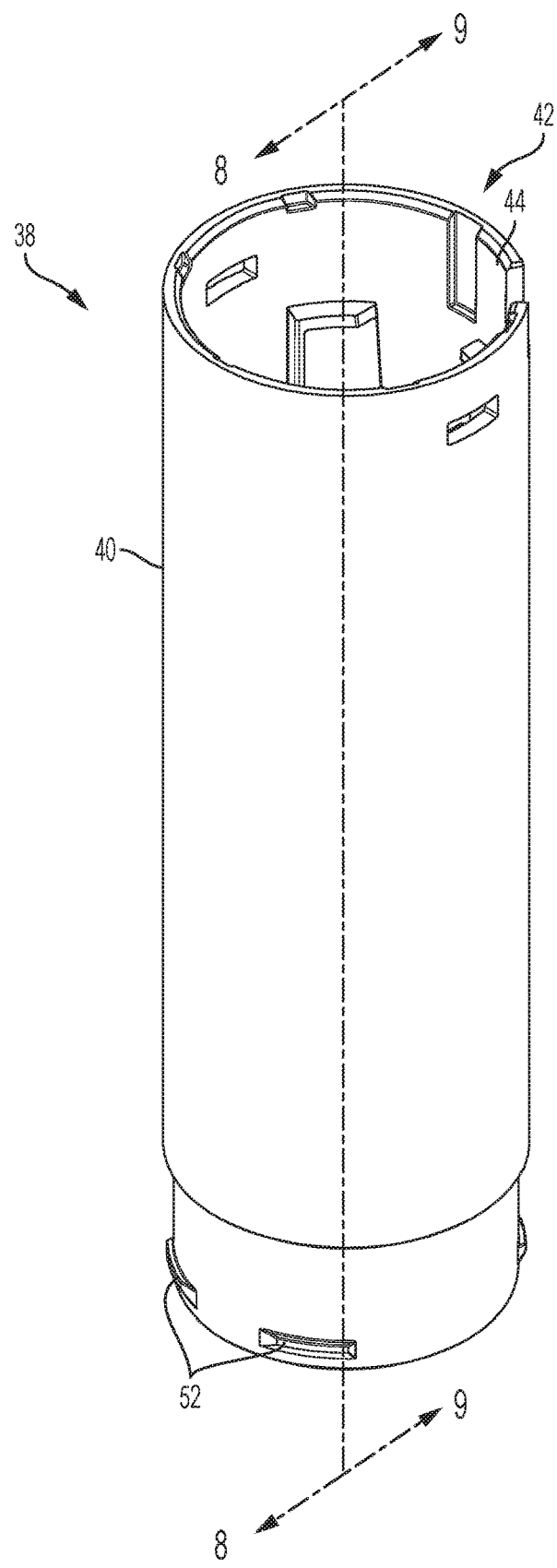
FIG. 7 is a top perspective view of a proximal housing portion of a housing of the therapeutic agent delivery system of FIG. 1.
Figure 8:
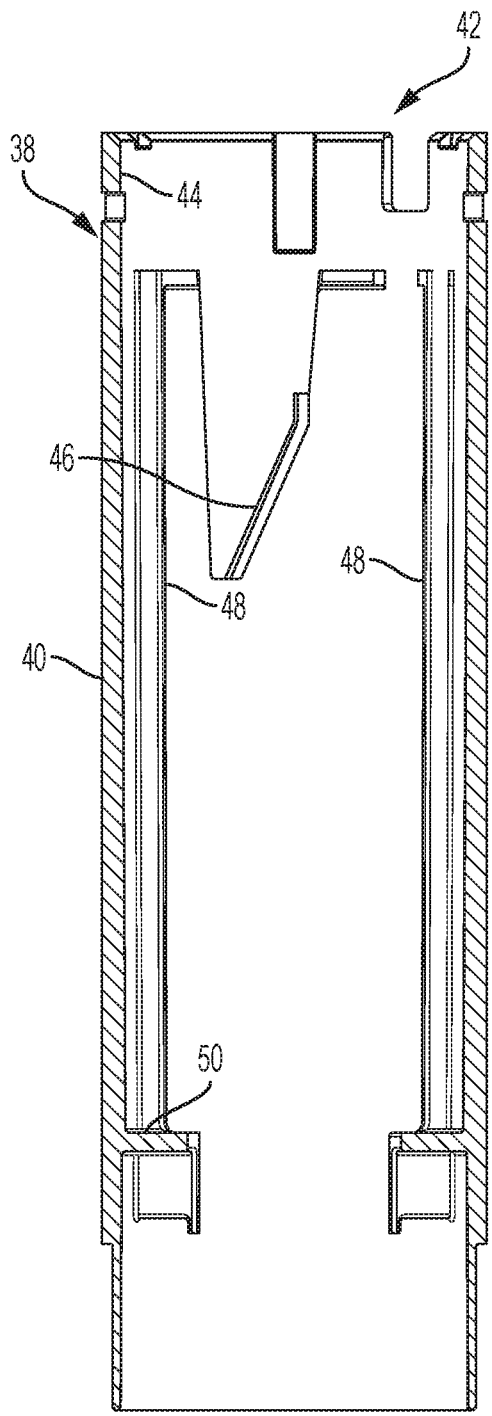
FIG. 8 is a longitudinal sectional view of the proximal housing portion along line 8-8 of FIG. 7.
Figure 9:
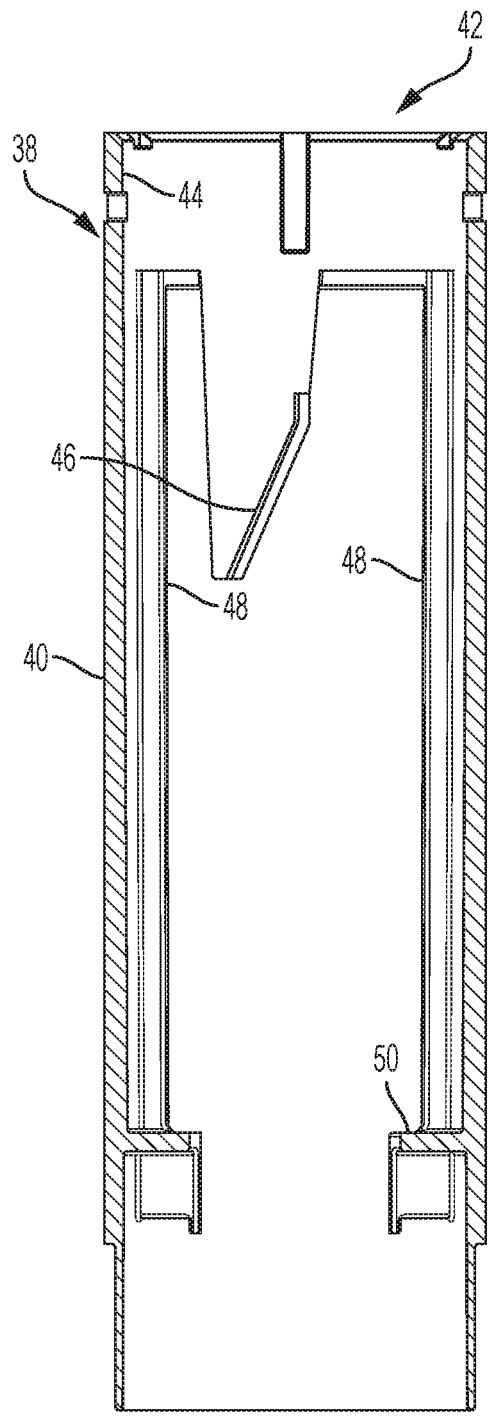
FIG. 9 is a longitudinal sectional view of the proximal housing portion along line 9-9 of FIG. 7.

FIGS. 7-9 illustrate a proximal housing portion 38 of the housing 12. The proximal housing portion 38 includes a main body 40 that has a generally cylindrical shape. The main body 40 includes an inner passageway 42 that carries other components of the therapeutic agent delivery system 10. Adjacent to the inner passageway 42, an inner surface 44 of the proximal housing portion 38 carries an actuation feature (illustratively, two helically extending ramps 46) that, as described in further detail below, selectively engage and facilitate actuating the therapeutic agent delivery assembly 16. The inner surface 44 of the proximal housing portion 38 carries a translation feature (illustratively, four axially extending ridges 48) that facilitates translation of the sleeve 24 in the inner passageway 42. The inner surface 44 also carries a biasing feature (illustratively, a radially-inwardly extending flange 50) that, as described in further detail below, engages a spring (shown elsewhere). The proximal housing portion 38 includes a coupling feature (illustratively, a plurality of snap connectors 52) for coupling to the distal housing portion 28. In other embodiments, different arrangements of the proximal housing portion 38 are possible. For example, the proximal housing portion 38 may be monolithically formed with the distal housing portion 28.

FIGS. 10-12 illustrate the sleeve 24 of the therapeutic agent delivery system 10. Illustratively, the sleeve 24 is formed of a conductive material (for example, a metal) to facilitate, as described in further detail below, operatively coupling components of an electronics assembly (shown elsewhere) of the therapeutic agent delivery system 10. The sleeve 24 includes a distal sleeve portion 54 that has a generally cylindrical shape. The distal sleeve portion 54 includes an inner passageway 56 that carries components of the therapeutic agent delivery assembly 16. The distal sleeve portion 54 includes a restraint feature (illustratively, two radially-outwardly extending tabs 58) for selectively engaging the restraint feature of the distal housing portion 28 (illustratively, the two radially-inwardly extending and inwardly deflectable tabs 36) and, as described in further detail below, selectively inhibiting translation of the sleeve 24 relative to the distal housing portion 28. As shown in FIG. 11, the tabs 58 taper radially-outwardly proceeding away from the distal end portion 26 (FIG. 1). The distal sleeve portion 54 couples to two proximally and axially extending arms 60. The axially extending arms 60 carry a translation feature (illustratively, four axially extending ridges 62) that engage the translation feature of the proximal housing portion 38 (illustratively, the four axially extending ridges 48) to facilitate translation and inhibit rotation of the sleeve 24 within the housing 12. The axially extending arms 60 also define, together with the therapeutic agent delivery assembly 16, a cam and slot mechanism that facilitates rotation of the therapeutic agent delivery assembly 16 relative to the housing 12 upon translation of the sleeve 24 relative to the housing 12. Illustratively, the axially extending arms 60 each include a slot 64 of the cam and slot mechanism, and the slots 64 translatably receive cams of the therapeutic agent delivery assembly 16 (shown elsewhere). The slots 64 illustratively include a helically extending proximal slot portion 66 and an axially extending distal slot portion 68. In other embodiments, different arrangements of the sleeve 24 are possible. For example, the slots 64 of the axially extending arms 60 may have different shapes, or the axially extending arms 60 may include cams instead of slots.

Figure 13:
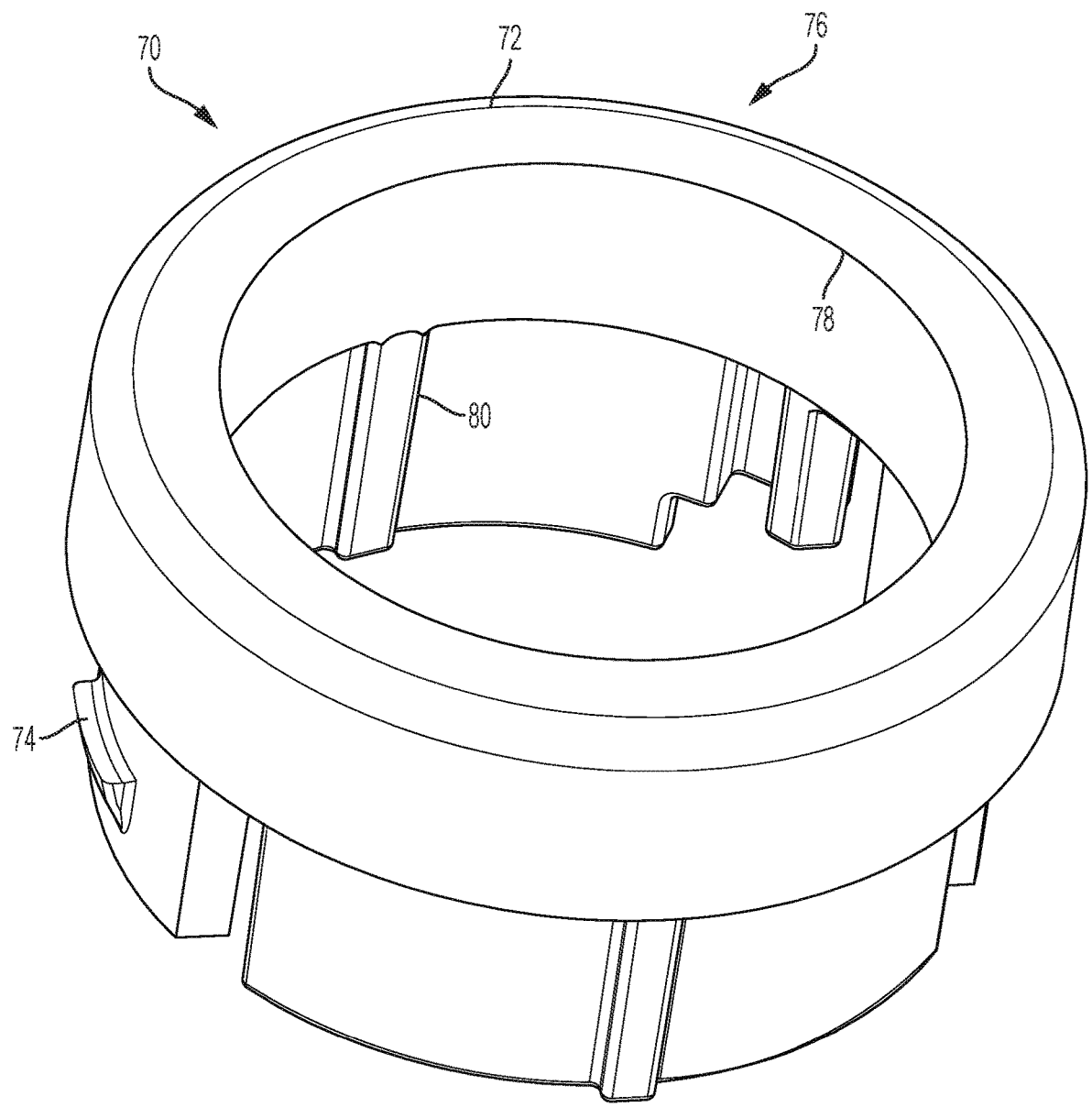
FIG. 13 is a top perspective view of a user input support of the therapeutic agent delivery system of FIG. 1.

FIG. 13 illustrates a user input support 70 of the therapeutic agent delivery system 10. The user input support 70 couples to the proximal housing portion 38 opposite the distal housing portion 28. The user input support 70 includes a main body 72, and the main body 72 carries a coupling feature (illustratively, a plurality of snap connectors 74) for coupling to the proximal housing portion 38. The main body 72 includes an inner passageway 76 in which the user input 22 is received. Adjacent to the inner passageway 76, an inner surface 78 of the user input support 70 carries a translation feature (illustratively, a plurality of axially extending ridges 80) that facilitates translation of the user input 22 relative to the user input support 70. In other embodiments, different arrangements of the user input support 70 are possible.

Figure 14:
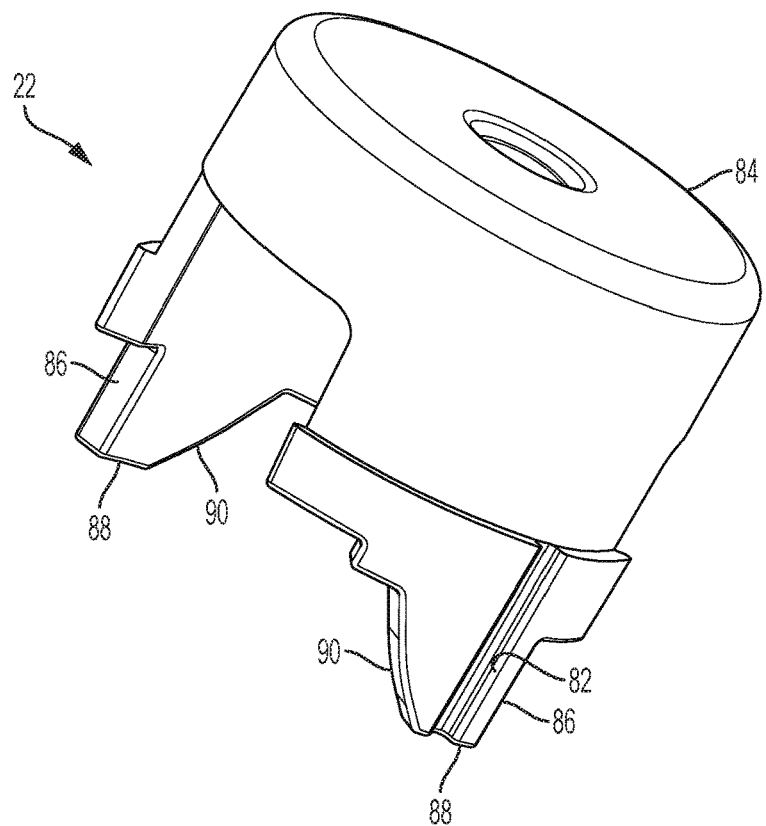
FIG. 14 is a top perspective view of a user input of the therapeutic agent delivery system of FIG. 1.

FIG. 14 illustrates the user input 22 of the therapeutic agent delivery system 10. The user input 22 includes a translation feature (illustratively, a plurality of axially extending channels 82) for engaging the translation feature of the user input support 70 (illustratively, the plurality of axially extending ridges 80) to facilitate translation of the user input 22 relative to the user input support 70 and the housing 12. Adjacent to the translation feature, the user input 22 includes an exposed portion 84 that is pressed by a user to translate the user input 22 relative to the user input support 70 and the housing 12. The user input 22 also includes an actuation feature that facilitates actuating the therapeutic agent delivery assembly 16. Illustratively, the actuation feature includes two arms 86 that are disposed opposite the exposed portion 84. Each of the arms 86 includes a restraint surface (illustratively, a circumferentially extending surface 88) and an actuation surface (illustratively, a helically extending surface 90). Interaction of the arms 86 with other components of the therapeutic agent delivery system 10 is described in further detail below. In other embodiments, different arrangements of the user input 22 are possible.

Figure 15:
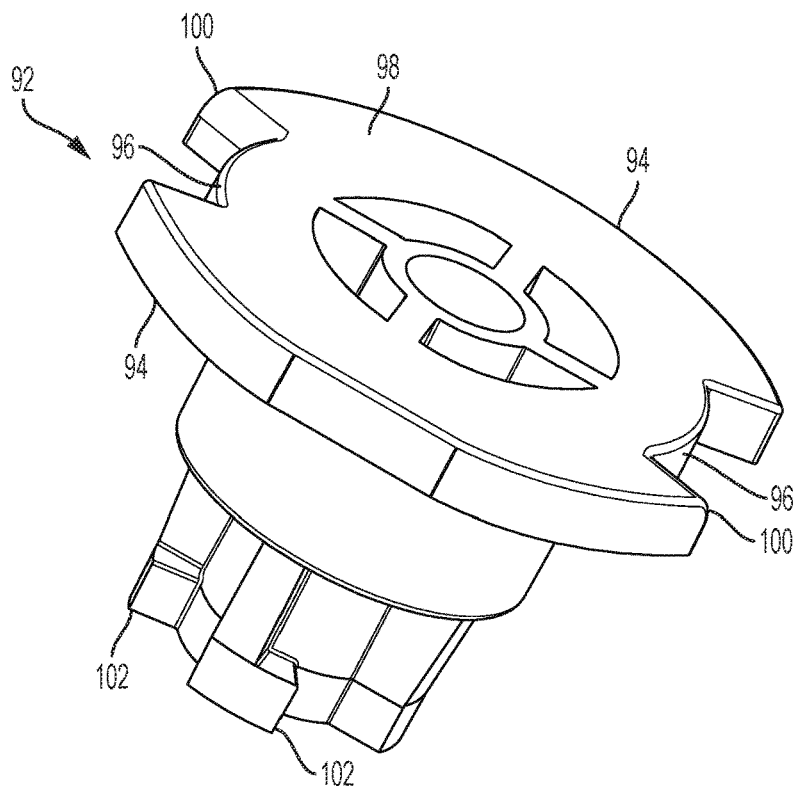
FIG. 15 is a top perspective view of an input restraint of the therapeutic agent delivery system of FIG. 1.
Figure 16:
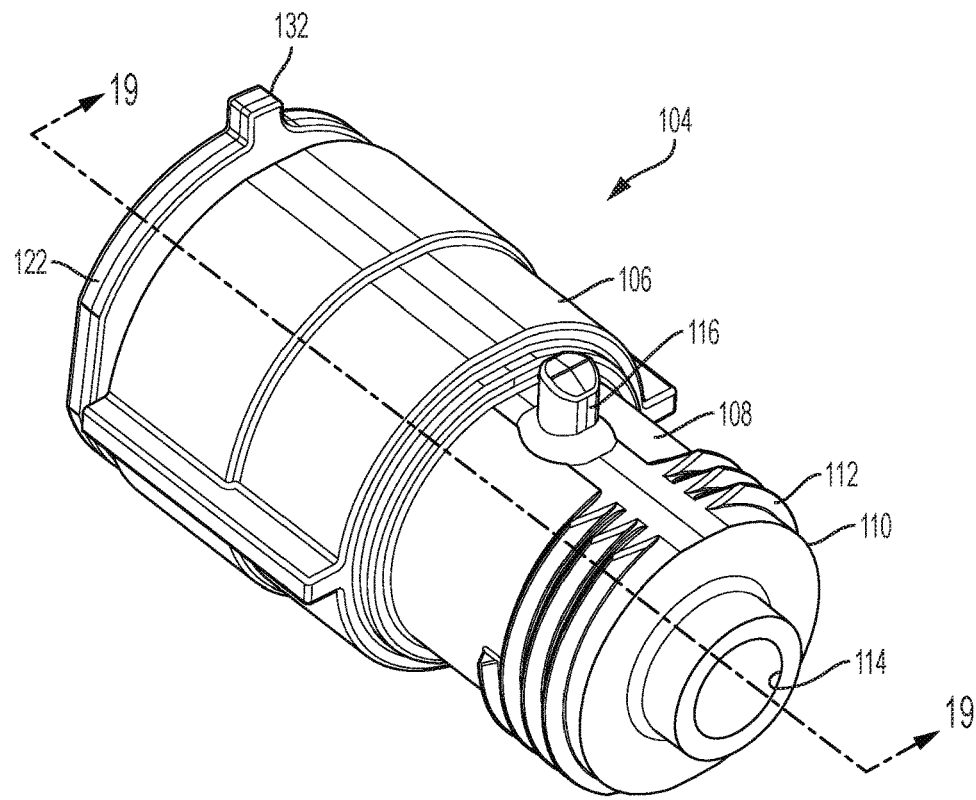
FIG. 16 is a bottom perspective view of a pressure generating actuator of a therapeutic agent delivery assembly of the therapeutic agent delivery system of FIG. 1.
Figure 17:
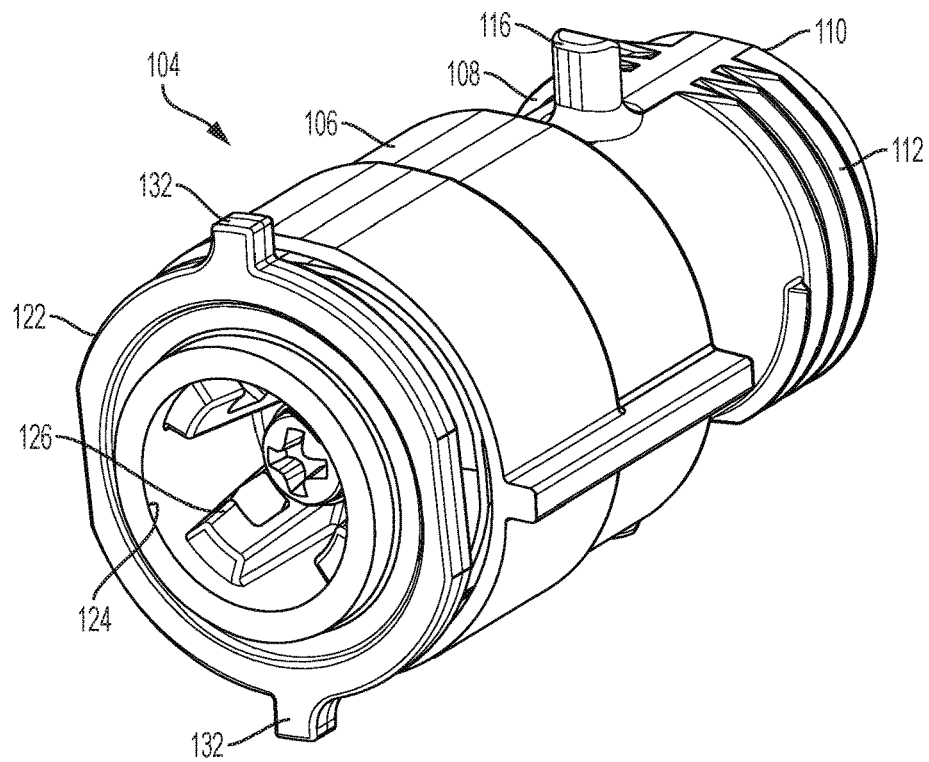
FIG. 17 is a top perspective view of the pressure generating actuator of FIG. 16.
Figure 18:
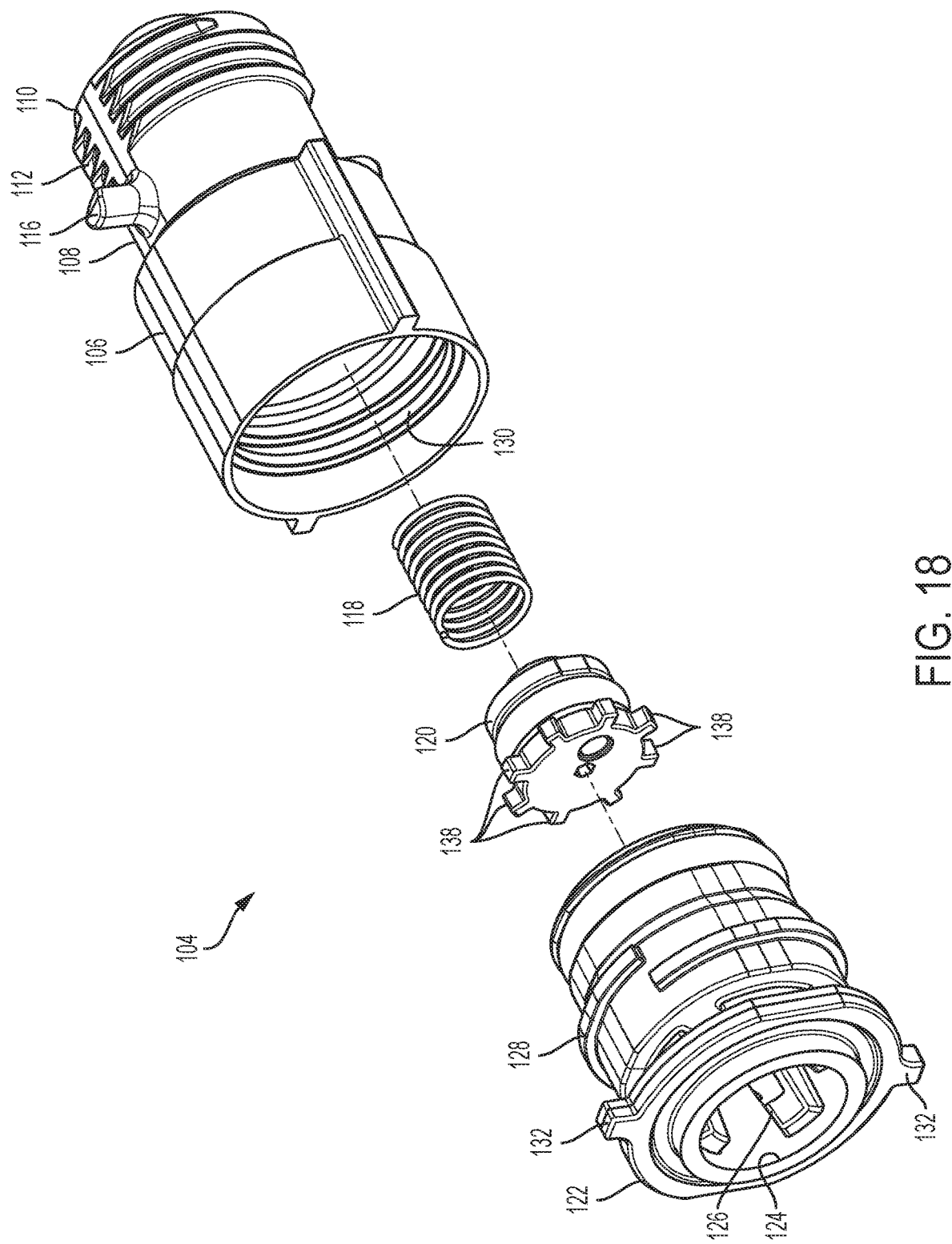
FIG. 18 is an exploded perspective view of the pressure generating actuator of FIG. 16.

FIG. 15 illustrates an input restraint 92 of the therapeutic agent delivery system 10. The input restraint 92 includes an actuation feature that is configured to interact with the actuation feature of the user input 22. Illustratively, the actuation feature of the input restraint 92 includes two partial flanges 94 and two openings 96 disposed between the partial flanges 94. Each of the partial flanges 94 includes a restraint surface (illustratively, a circumferentially extending surface 98) that, in certain situations and as described in further detail below, engages one of the restraint surfaces 88 of the user input 22 to inhibit translation of the user input 22 relative to the housing 12. Each of the partial flanges 94 also includes an actuation surface (illustratively, a rounded corner 100 adjacent to one of the openings 96) that, in certain situations, engages one of the actuation surfaces 90 of the user input 22 to facilitate rotating the input restraint 92 relative to the housing 12 upon translating the user input 22 relative to the housing 12. Opposite the actuation feature, the input restraint 92 includes a detachable coupling feature (illustratively, a plurality of ledges 102 or radially-outwardly extending L-shaped protrusions 102) that detachably couples the input restraint 92 to the therapeutic agent delivery assembly 16. In other embodiments, different arrangements of the input restraint 92 are possible.

FIG. 16-19 illustrate a pressure generating actuator 104 of the therapeutic agent delivery assembly 16. Generally, the pressure generating actuator 104 is actuated by the user input 22, via the input restraint 92, to facilitate mixing of internally-carried chemical reagents, which generates one or more pressurized fluids (for example, one or more gases). Examples of suitable reagents and generated gases are provided below. As described in further detail below, the pressurized fluid(s) are delivered to and facilitate movement of other components of the therapeutic agent delivery assembly 16.

The pressure generating actuator 104 includes a first mixing chamber 106 and a second mixing chamber 108, which are illustratively monolithically formed with each other. At an outlet end portion 110, the mixing chambers 106, 108 include an outlet coupling feature (illustratively, an externally threaded surface 112) for coupling to another component of the therapeutic agent delivery assembly 16. The outlet end portion 110 also includes an actuator outlet 114 through which pressurized fluid is discharged from the pressure generating actuator 104. The mixing chambers 106, 108 also define, together with the sleeve 24, the cam and slot mechanism. Illustratively, the mixing chambers 106, 108 carry radially-outwardly extending fingers or cams 116 of the cam and slot mechanism, and the cams 116 are translatably received in the slots 64 of the sleeve 24. In other embodiments, different arrangements are possible. For example, mixing chambers 106, 108 may include slots instead of cams.

Figure 19:
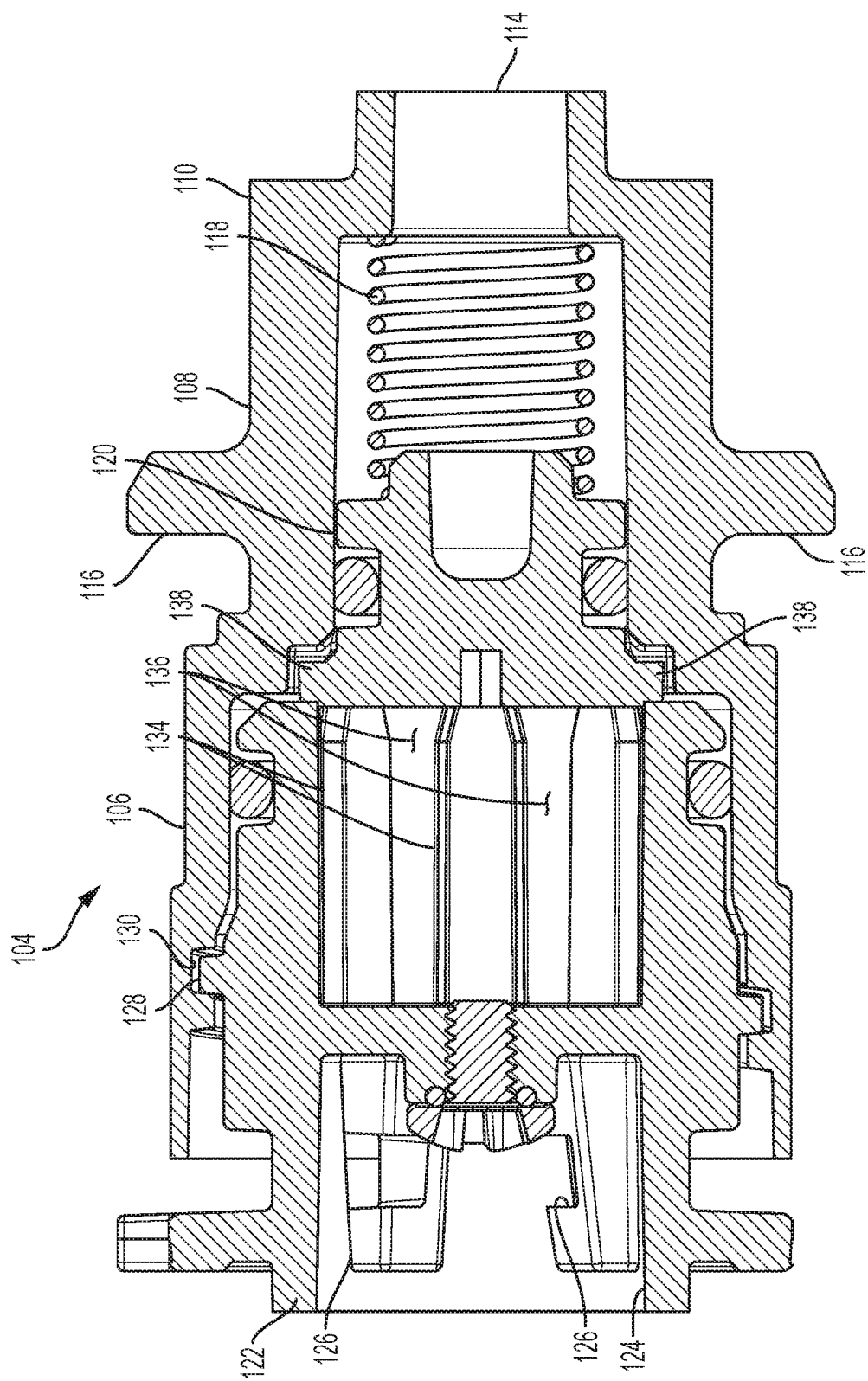
FIG. 19 is a longitudinal sectional view of the pressure generating actuator along line 19-19 of FIG. 16.

Internally, the mixing chambers 106, 108 carry an actuator spring 118, a mixing piston 120, and a rotatable shuttle 122 in an axially stacked arrangement. The rotatable shuttle 122 includes a recess 124, and the recess 124 carries a detachable coupling feature (illustratively, a plurality of ledges 126 or radially-outwardly extending L-shaped protrusions 126) that engages the detachable coupling feature of the input restraint 92 (illustratively, the plurality of ledges 102). The first mixing chamber 106 and the shuttle 122 form a helical coupling for movably coupling to each other. Illustratively, the shuttle 122 includes a helically extending ridge 128 and the first mixing chamber 106 includes a helically extending groove 130 that receives the ridge 128. The shuttle 122 includes an actuation feature (illustratively, two radially-outwardly extending fingers 132) that, as described in further detail below, engage and are driven by the actuation feature of the proximal housing portion 38 (illustratively, the two helically extending ramps 46). Internally, the shuttle 122 includes a first restraining feature (illustratively, eight radially-inwardly extending tabs 134) that engages the mixing piston 120. Illustratively, the shuttle 122 also includes channels 136 disposed between adjacent tabs 134. The mixing piston 120 includes a second restraining feature (illustratively, eight radially-outwardly extending tabs 138) that engages the first restraining feature of the shuttle 122. Initially and as shown in FIG. 19, the first restraining feature engages the second restraining feature (illustratively, the radially-inwardly extending tabs 134 of the shuttle 122 are angularly aligned with and engage the radially-outwardly extending tabs 138 of the mixing piston 120) to hold the mixing piston 120 in a position between the first mixing chamber 106 and the second mixing chamber 108. The mixing piston 120 thereby maintains separation of reagents in the first mixing chamber 106 and the second mixing chamber 108. Initially the actuator spring 118 is also compressed within the second mixing chamber 108 against the mixing piston 120. In a subsequent configuration, as described in further detail below, the shuttle 122 rotates relative to the first mixing chamber 106 and the second mixing chamber 108 to disengage the first restraining feature from the second restraining feature (illustratively, the radially-inwardly extending tabs 134 of the shuttle 122 are angularly misaligned with, or angularly offset from, the radially-outwardly extending tabs 138 of the mixing piston 120, and the channels 136 are angularly aligned with the radially-outwardly extending tabs 138 of the mixing piston 120). As a result, the actuator spring 118 expands and moves the mixing piston 120 into the shuttle 122 and the first mixing chamber 106, which permits the reagents in the first mixing chamber 106 and the second mixing chamber 108 to mix. Mixing of the reagents generates one or more pressurized fluids (for example, one or more gases), and the pressurized fluid(s) are delivered to other components of the therapeutic agent delivery assembly 16. The reagents may mix in only first mixing chamber 106 or in both mixing chambers 106, 108.

In some embodiments, pressure generating actuators 104 have different structures. For example, suitable pressure generating actuators 104 include those described in: U.S. Pat. No. 9,795,740 titled "Chemical Engines and Methods for Their Use, Especially in the Injection of Highly Viscous Fluids"; International PCT Application No. PCT/US2018/017547, titled "Processes and Devices for Delivery of Fluid by Chemical Reaction" and filed Feb. 9, 2018; and International PCT Application No. PCT/US2018/049048, titled "System for Controlling Gas Generation with a Drug Delivery Device" and filed on Aug. 31, 2018, the disclosures of which are expressly incorporated herein by reference in their entirety.

Any suitable chemical reagent or reagents can be used to generate one or more pressurized fluids in pressure generating actuators 104 of the present disclosure. Examples of generated gases include carbon dioxide gas, nitrogen gas, oxygen gas, chlorine gas, etc. Desirably, the generated gas is inert and non-flammable. The amount of gas needed to facilitate movement of other components of the therapeutic agent delivery assembly 16 may impact the type, amount, and concentration of each reagent used in pressure generating actuators 104. The reagents may be in dry form (for example, powdered form, tablet form, and/or low-density freeze-dried solid form) and/or in liquid form (for example, a solution, colloid, or stable or non-stable suspension).

In one exemplary embodiment, a bicarbonate (which may be present in dry form) reacts with an acid (which may be present in liquid form) to produce carbon dioxide gas in pressure generating actuators 104. Examples of suitable bicarbonates include sodium bicarbonate, potassium bicarbonate, and ammonium bicarbonate. Other ingredients may also be present along with the bicarbonates, such as diatomaceous earth. Examples of suitable acids include acetic acid, citric acid, potassium bitartrate, disodium pyrophosphate, and calcium dihydrogen phosphate. In one particular example, the bicarbonate is potassium bicarbonate and the acid is aqueous citric acid, which may react to produce carbon dioxide gas and a liquid mixture of water and dissolved potassium citrate.

In some embodiments, other reactions may be used. In one example, a metal carbonate, such as copper carbonate or calcium carbonate, is thermally decomposed to produce carbon dioxide gas and the corresponding metal oxide in pressure generating actuators 104. In another example, 2,2'-azobisisobutyronitrile (AIBN) is heated to produce nitrogen gas in pressure generating actuators 104. In yet another example, enzymes (for example yeast) are reacted with sugar to produce carbon dioxide gas in pressure generating actuators 104. Some substances readily sublime, going from solid to gas. Such substances include but are not limited to naphthalene and iodine. In still yet another example, hydrogen peroxide is decomposed with catalysts such as enzymes (for example catalase) or manganese dioxide to produce oxygen gas in pressure generating actuators 104. In still yet another example, silver chloride is decomposed through exposure to light to generate a gas in pressure generating actuators 104. Suitable reagents, chemical formulations, and reactions are further described in the above-incorporated U.S. Pat. No. 9,795,740, International PCT Application No. PCT/US2018/017547, and International PCT Application No. PCT/US2018/049048.

Figure 20:
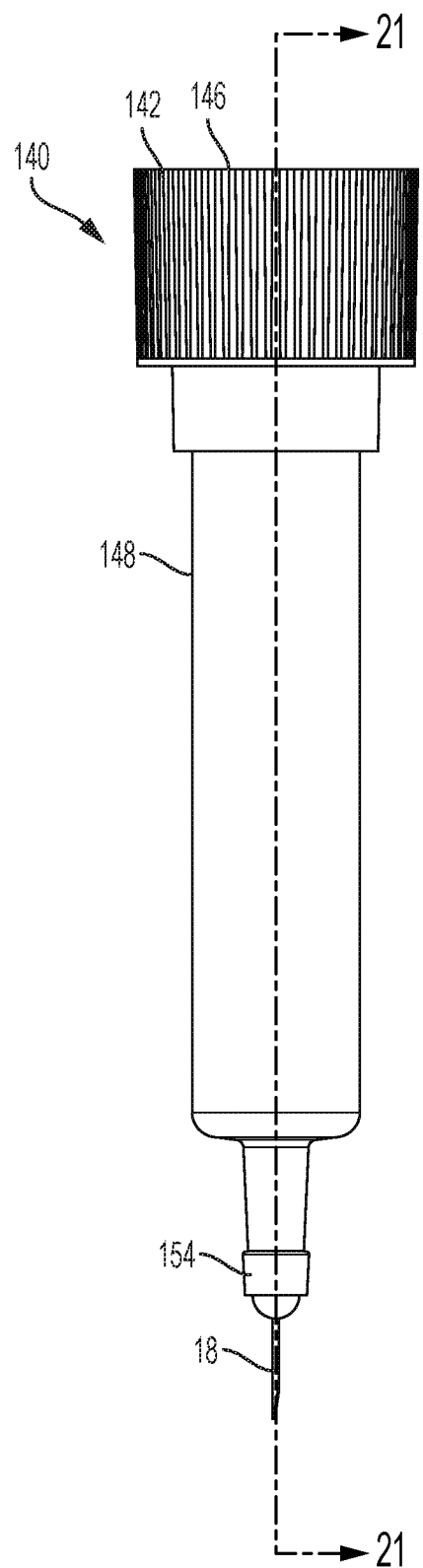
FIG. 20 is a side view of a syringe assembly of the therapeutic agent delivery assembly of the therapeutic agent delivery system of FIG. 1.
Figure 21:
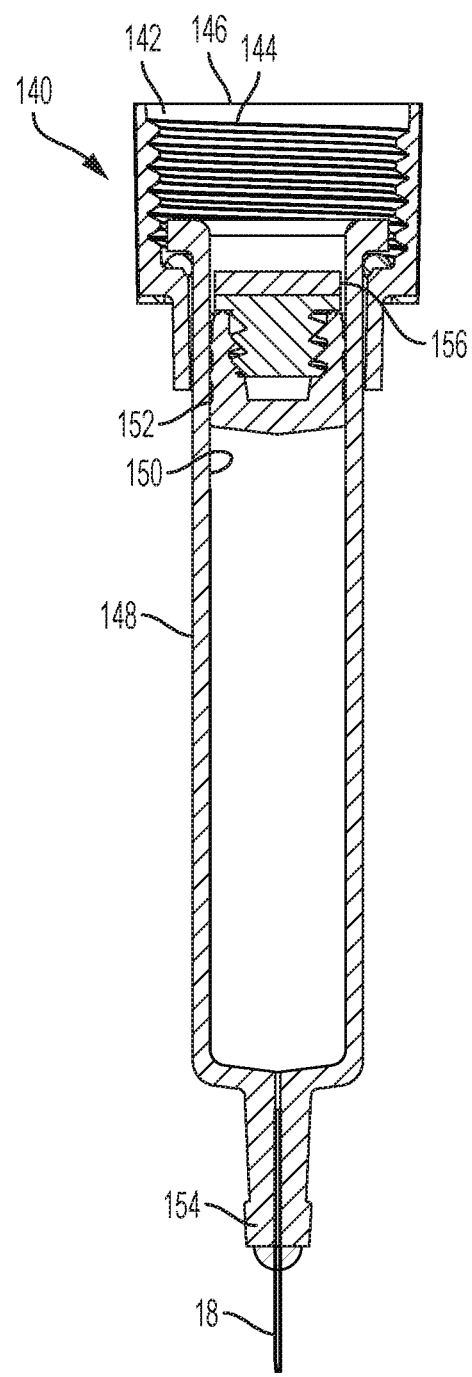
FIG. 21 is a longitudinal sectional view of the syringe assembly along line 21-21 of FIG. 20.

FIGS. 20-21 illustrate a syringe assembly 140 of the therapeutic agent delivery assembly 16. The syringe assembly 140 includes an inlet portion 142, and the inlet portion 142 includes an inlet coupling feature (illustratively, an internally threaded surface 144) that couples to the outlet coupling feature of the pressure generating actuator 104 (illustratively, the externally threaded surface 112). The inlet portion 142 also includes an inlet 146 that receives pressurized fluid(s) from the outlet 114 of the pressure generating actuator 104. The inlet portion 142 couples to a syringe chamber 148, and the syringe chamber 148 includes a syringe passageway 150 that receives the pressurized fluid(s) from the inlet portion 142. The syringe passageway 150 carries a syringe piston 152, and the syringe piston 152 translates away from the inlet portion 142 and towards an outlet portion 154 of the syringe assembly 140 when the syringe passageway 150 receives the pressurized fluid(s). Illustratively and as described in further detail below, the syringe piston 152 carries a magnetic component 156 that facilitates determining the position of the syringe piston 152 in the syringe passageway 150. The syringe passageway 150 also carries a therapeutic agent (illustratively, 2.25 mL of the therapeutic agent, although other suitable volumes, including, for example, 2.08 mL, 1.08 mL, or 0.58 mL may alternatively be carried) between the syringe piston 152 and the outlet portion 154, more specifically the needle 18. As such, translation of the syringe piston 152 in the syringe passageway 150 causes the needle 18 to discharge the therapeutic agent therefrom. In other embodiments, different arrangements are possible. For example, the inlet portion 142 and the syringe chamber 148 may be monolithically formed with each other, or the syringe assembly 140 could be replaced by another type of therapeutic agent container, such as a bellows or bladder structure.

Figure 22:
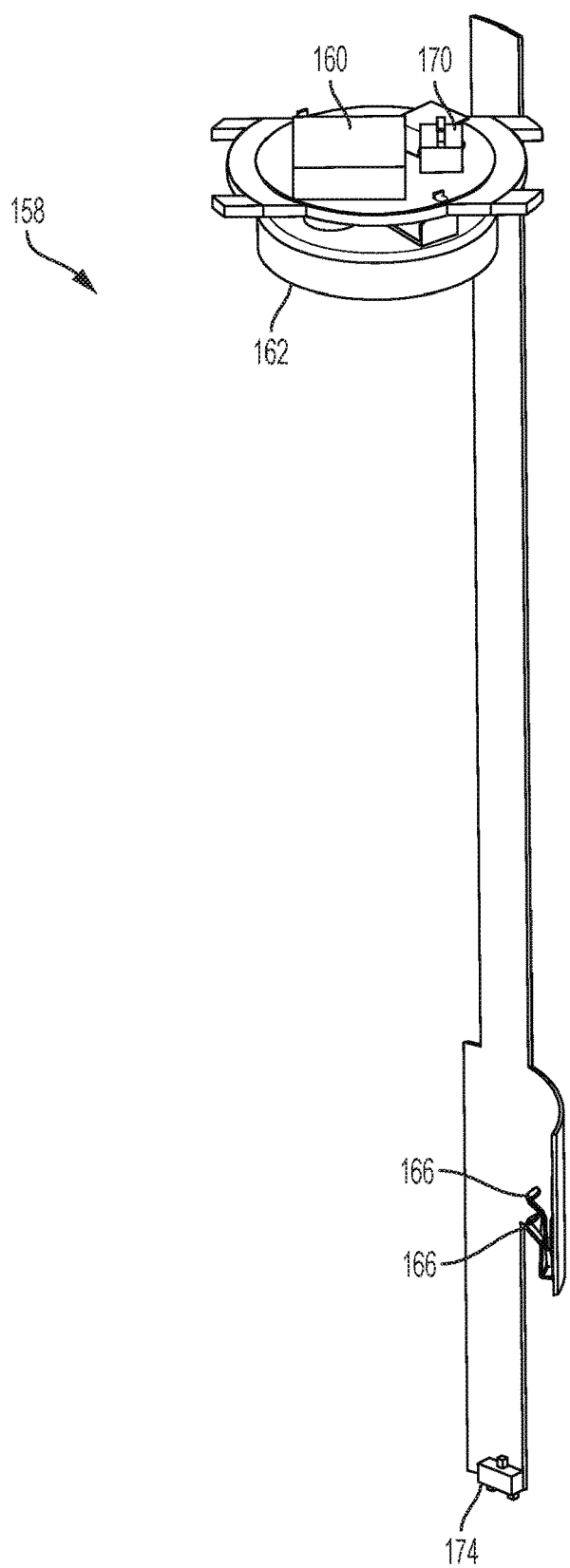
FIG. 22 is a top perspective view of an electronics assembly of the therapeutic agent delivery system of FIG. 1.
Figure 23:
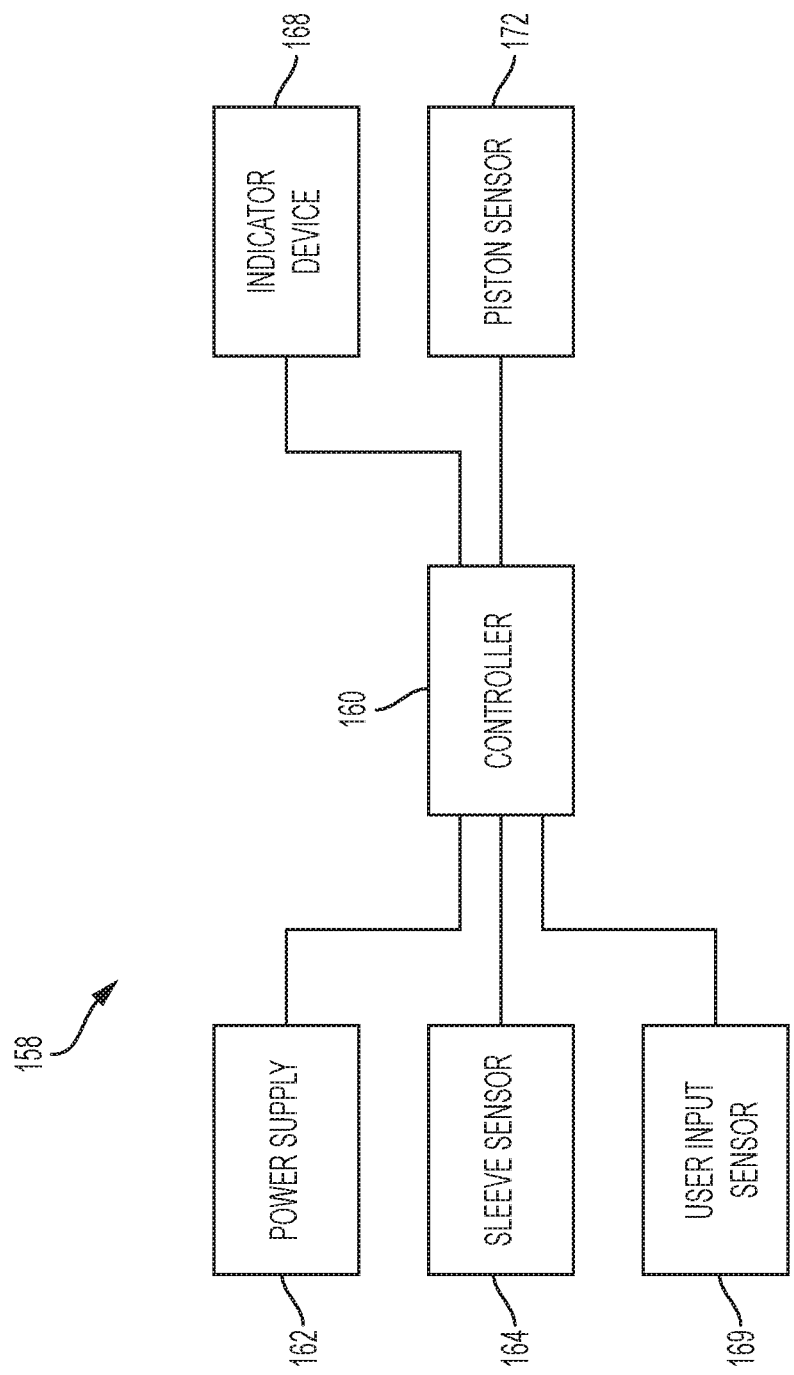
FIG. 23 is a schematic representation of the electronics assembly of FIG. 22.

FIGS. 22-23 illustrate an electronics assembly 158 of the therapeutic agent delivery system 10. The electronics assembly 158 includes an electronic controller 160 that is operatively coupled to and receives power from a power supply 162 (illustratively, a battery). The controller 160 is operatively coupled to a sleeve sensor 164 that determines if the sleeve 24 has been translated relative to the housing 12 and the user input 22 is thereby "unlocked" (illustratively, two electrical contacts 166 that engage the sleeve 24 and thereby close a circuit when the sleeve 24 translates relative to the housing 12). The controller 160 is operatively coupled to an indicator device 168 (including, for example, visual and/or audible indicators) that indicates the status of the system 10 (for example, that the sleeve 24 has been translated relative to the housing 12 and the user input 22 is thereby unlocked). The controller 160 is operatively coupled to a user input sensor 169 (illustratively, an electrical switch 170) that determines if the user input 22 has been actuated. The indictor device 210 may provide an indication (for example, a visual and/or audible indication) if the user input 22 has been actuated. The controller 160 is operatively coupled to a piston sensor 172 that is configured to determine the position of the syringe piston 152 in the syringe chamber 148 (for example, to determine if the syringe piston 152 has been moved toward the syringe outlet portion 154, thereby indicating that the therapeutic agent has been discharged from the needle 18). Illustratively, the piston sensor 172 is a hall effect sensor 174 that is configured to sense the magnetic component 156 carried by the syringe piston 152. In other embodiments, the piston sensor 172 may be an optical sensor. The indictor device 210 may provide an indication (for example, a visual and/or audible indication) if the magnetic component 156 and the syringe piston 152 have been moved toward the syringe outlet portion 154.

Figure 24:
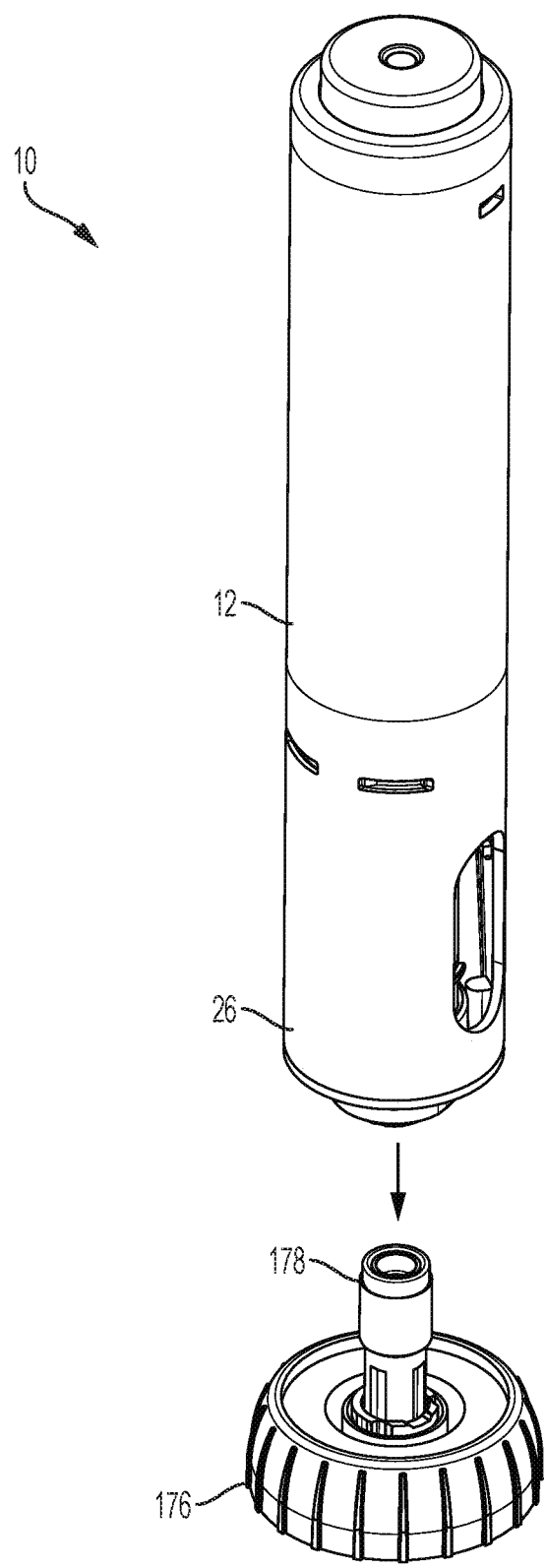
FIG. 24 is a top perspective view of an end cap and a needle cover being removed from the distal end portion of the therapeutic agent delivery system of FIG. 1.
Figure 27:
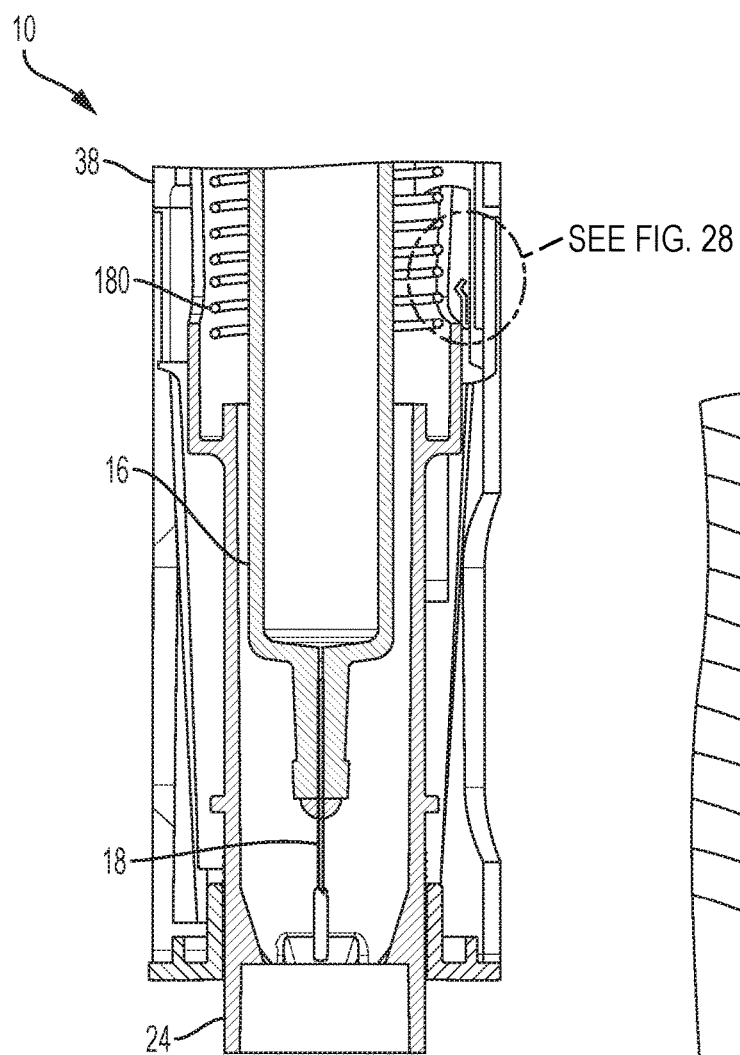
FIG. 27 is a longitudinal sectional partial view of the therapeutic agent delivery system of FIG. 1 in the first configuration; the housing is shown in hidden lines to illustrate internal components.
Figure 28:
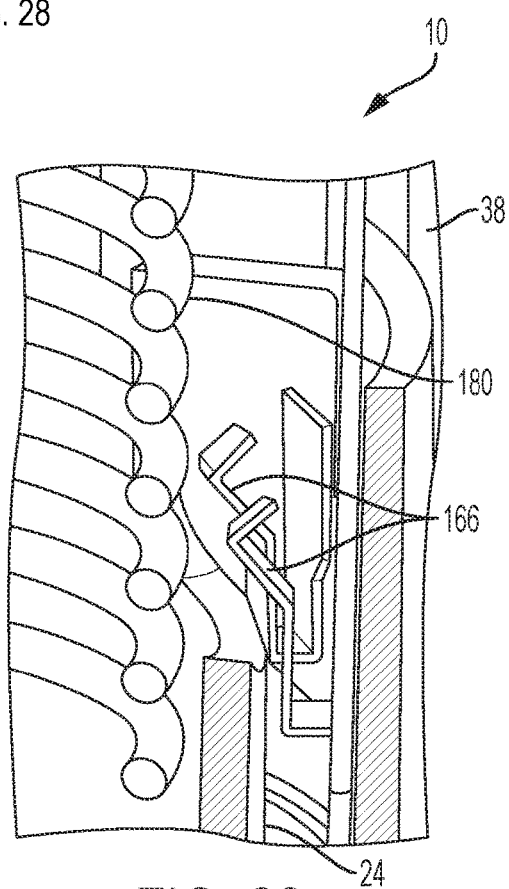
FIG. 28 is a detail side perspective view of the therapeutic agent delivery system within line 28-28 of FIG. 27 and in the first configuration.

Illustratively, actuation of the therapeutic agent delivery system 10 is as follows. As illustrated in FIG. 24, an end cap 176 and a needle cover 178 are removed from the distal end portion 26 of the therapeutic agent delivery system 10. FIGS. 25-28 illustrate the therapeutic agent delivery system 10 in a first configuration (which may also be referred to as a "locked" configuration). In the first configuration, the sleeve 24 is disposed in an exposed configuration (that is, the sleeve 24 partially extends from the distal housing portion 28), and an extension spring 180 compressed between the sleeve 24 and the proximal housing portion 38 (see FIGS. 27 and 28) urges the sleeve 24 to remain in the exposed configuration. In the first configuration and as shown specifically in FIG. 25, the cams 116 of the pressure generating actuator 104 are disposed in the proximal slot portions 66 of the sleeve 24. In the first configuration and as shown specifically in FIG. 26, the input restraint 92 is disposed in a first rotational configuration relative to the user input 22 and the housing 12. In the first rotational configuration, the input restraint 92 inhibits actuation of the user input 22 due to contact between the restraint surfaces 98 of the input restraint 92 and the restraint surfaces 88 of the user input 22. In the first configuration and as shown specifically in FIG. 27, the therapeutic agent delivery assembly 16 is disposed in the stowed configuration (illustratively, a configuration in which the needle 18 is disposed entirely within the housing 12). In the first configuration and as shown specifically in FIG. 28, the sleeve 24 is disposed apart from the electrical contacts 166.

Figures 29, 30:
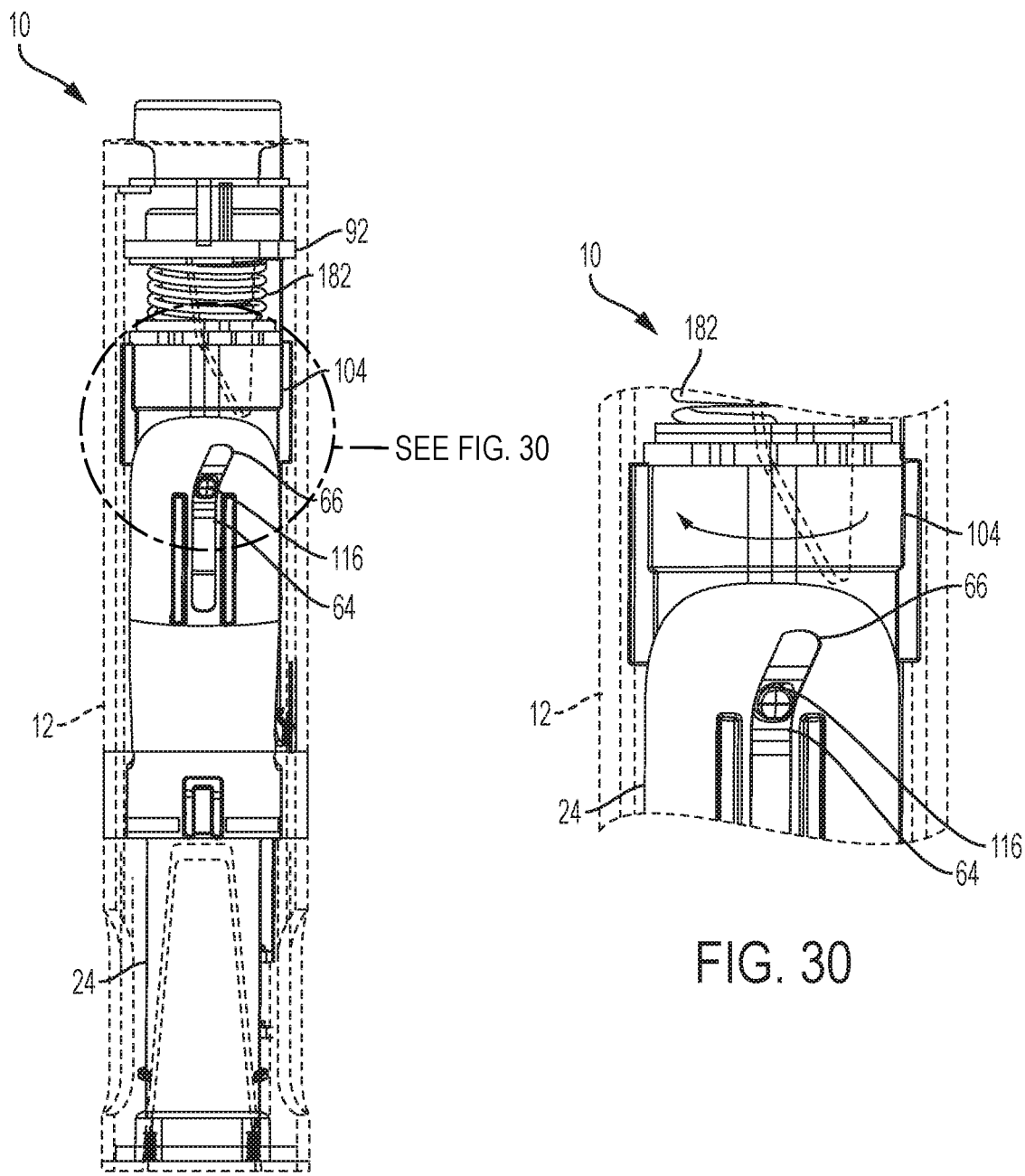
FIG. 29 is a side perspective view of the therapeutic agent delivery system of FIG. 1 in a second configuration; the housing is shown in hidden lines to illustrate internal components.
FIG. 30 is a detail top perspective view of the therapeutic agent delivery system within line 30-30 of FIG. 29 and in the second configuration.
Figure 31:
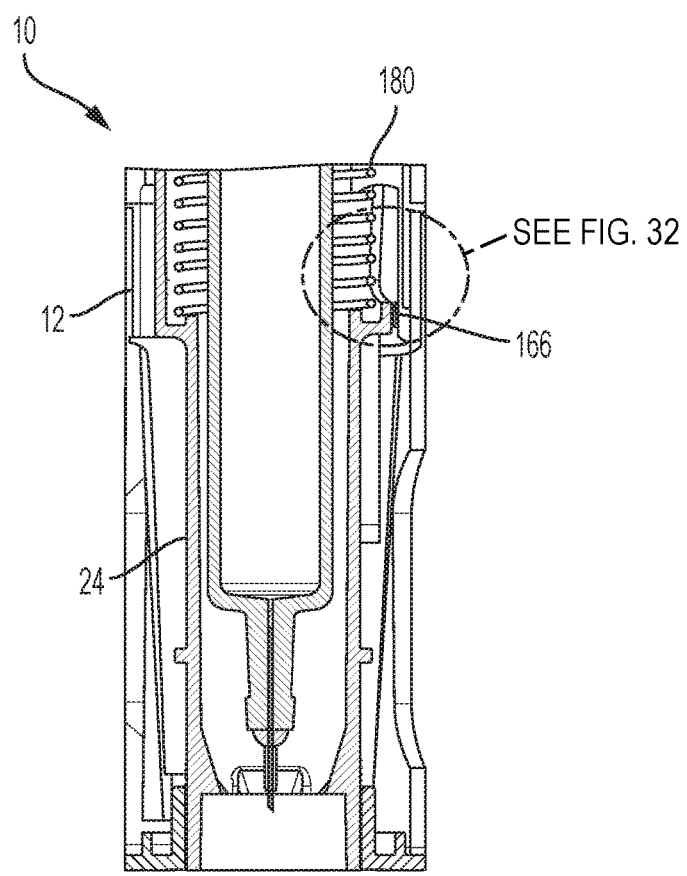
FIG. 31 is a longitudinal sectional partial view of the therapeutic agent delivery system of FIG. 1 in the second configuration; the housing is shown in hidden lines to illustrate internal components.
Figure 32:
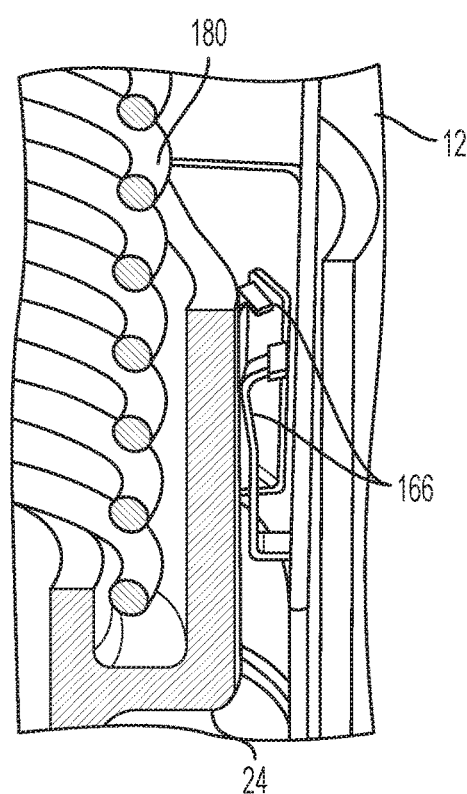
FIG. 32 is a detail side perspective view of the therapeutic agent delivery system within line 32-32 of FIG. 31 and in the second configuration.

FIGS. 29-30 illustrate the therapeutic agent delivery system 10 in a second configuration (which may also be referred to as an "unlocked" configuration). The therapeutic agent delivery system 10 moves from the first configuration to the second configuration upon pushing or pressing the sleeve 24 into a surface (for example, the skin of a subject) and translating the sleeve 24 relative to the housing 12 from the exposed configuration to a retracted configuration (illustratively, a configuration in which the sleeve 24 is disposed entirely within the housing 12). As shown specifically in FIGS. 29 and 30, translating the sleeve 24 from the exposed configuration to the retracted configuration causes relative movement of the cams 116 of the pressure generating actuator 104 and the slots 64 of the sleeve 24. More specifically, the cams 116 translate in the helically extending proximal portions 66 of the slots 64. This translation causes the pressure generating actuator 104, a deployment spring 182 compressed between the pressure generating actuator 104 and the input restraint 92, and the input restraint 92 to rotate relative to the housing 12 from the first rotational configuration to a second rotational configuration. In the second configuration and as shown specifically in FIGS. 31 and 32, the sleeve 24 engages the electrical contacts 166 and thereby closes a circuit. Upon closure of the circuit, the indicator device 168 may provide an indication (for example, visual and/or audible indications). In the second configuration, the therapeutic agent delivery system 10 may be returned to the first configuration by moving the therapeutic agent delivery system 10 apart from the surface (more specifically, by permitting the extension spring 180 to expand and move the sleeve 24 to the exposed configuration).

Figure 33:
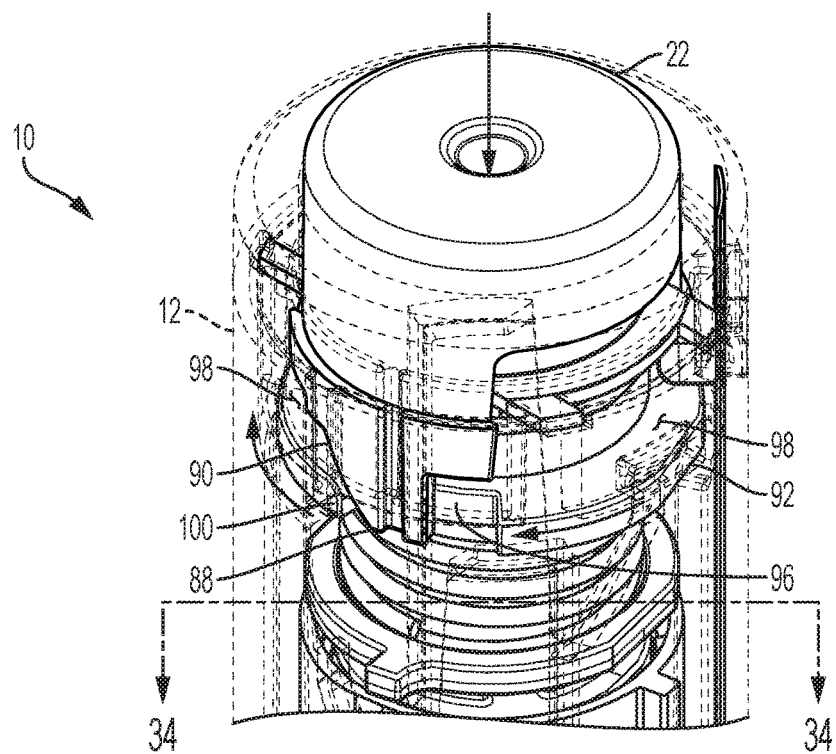
FIG. 33 is a detail top perspective view of the therapeutic agent delivery system of FIG. 1 upon actuating the user input; the housing is shown in hidden lines to illustrate internal components.
Figure 34:
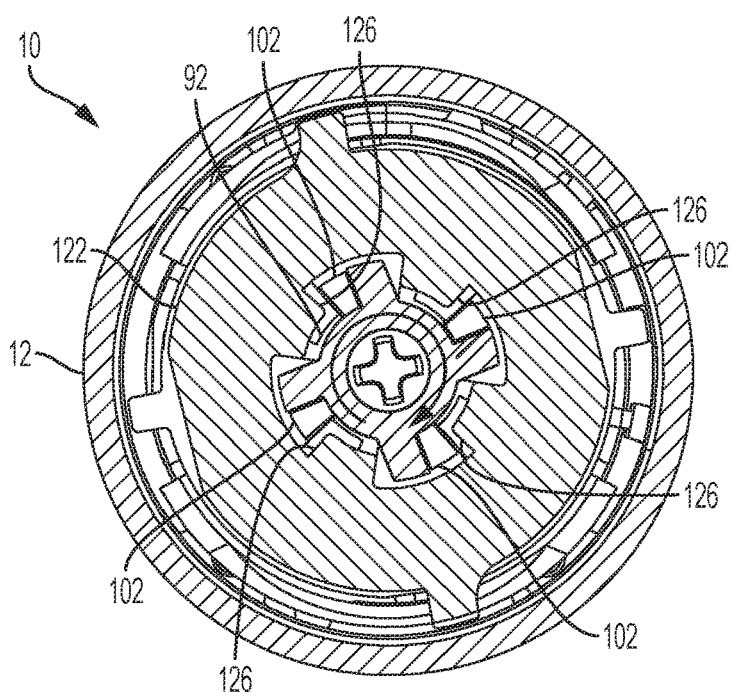
FIG. 34 is a cross sectional view of the therapeutic agent delivery system along line 34-34 of FIG. 33 upon actuating the user input.

Turning to FIGS. 33-34, in the second configuration the restraint surfaces 98 of the input restraint 92 are angularly misaligned with the restraint surfaces 88 of the user input 22, and the openings 96 of the input restraint 92 are angularly aligned with the restraint surfaces 88 of the user input 22. As such, the user input 22 may be actuated (illustratively, by translating the user input 22 relative to the housing 12 in a direction that is substantially parallel to the longitudinal axis 14 (that is, parallel±5 degrees)), which causes the actuation surfaces 90 of the user input 22 to engage the actuation surfaces 100 of the input restraint 92. The user input 22 thereby rotates the input restraint 92 from the second rotational configuration to a third rotational configuration, which causes, as shown specifically in FIG. 34, the ledges 102 of the input restraint 92 to slide over and disengage the ledges 126 of the shuttle 122. The user input 22 may also actuate the switch 170, and the indicator device 168 may provide an indication (for example, visual and/or audible indications).

Figure 35:
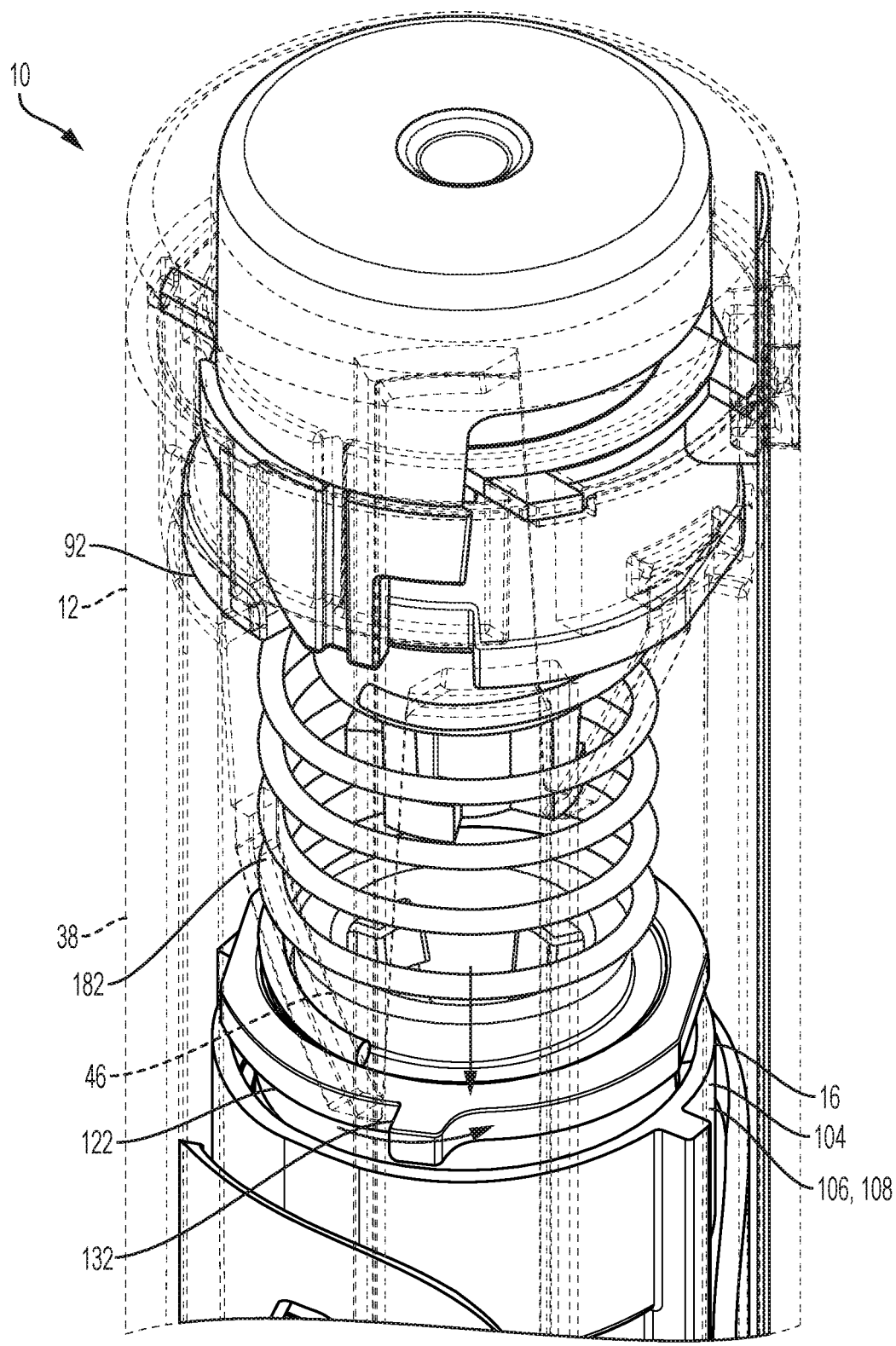
FIG. 35 is a detail top perspective view of the therapeutic agent delivery system of FIG. 1 upon a deployment spring expanding and moving the therapeutic agent delivery assembly distally relative to the housing; the housing is shown in hidden lines to illustrate internal components.
Figure 36:
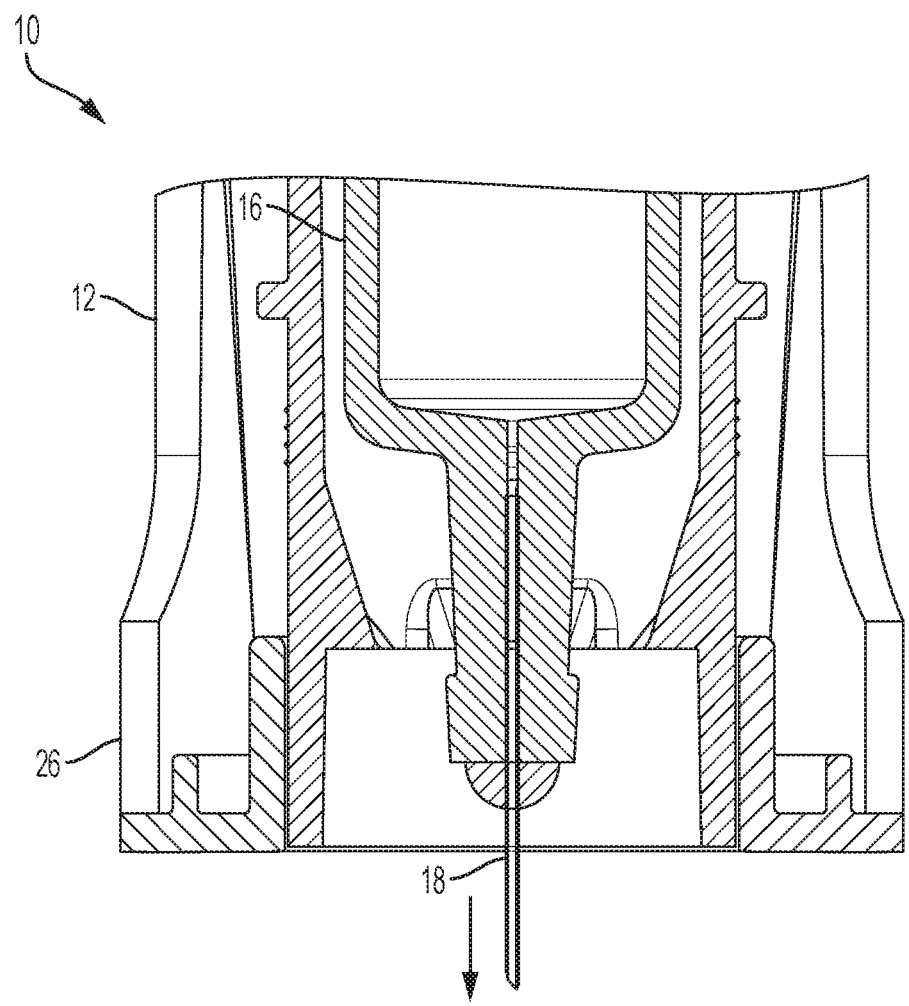
FIG. 36 is a longitudinal sectional partial view of the therapeutic agent delivery system of FIG. 1 upon the therapeutic agent delivery assembly moving to a deployed configuration.

As shown in FIG. 35, the deployment spring 182 is relatively unconstrained upon disengagement of the input restraint 92 and the shuttle 122. As such, the deployment spring 182 expands and pushes the therapeutic agent delivery assembly 16 distally relative to the housing 12. As shown in FIG. 36, the therapeutic agent delivery assembly 16 thereby moves from the stowed configuration to the deployed configuration (illustratively, a configuration in which the needle 18 is partially exposed at the distal end portion 26 of the housing 12 and configured to engage the subject and deliver the therapeutic agent to the subject). Illustratively, the needle 18 translates from the stowed configuration to the deployed configuration in a direction that is substantially parallel to the longitudinal axis 14 (that is, parallel±5 degrees). Referring again to FIG. 35, translation of the therapeutic agent delivery assembly 16 distally relative to the housing 12 also causes the radially-outwardly extending fingers 132 of the shuttle 122 to engage and slide over the helically extending ramps 46 of the proximal housing portion 38. This engagement causes the shuttle 122 to rotate relative to the mixing chambers 106, 108 of the pressure generating actuator 104 (illustratively, about an axis that is substantially parallel to the longitudinal axis 14 (that is, parallel±5 degrees)), which actuates the pressure generating actuator 104. More specifically and as illustrated in FIG. 37, the rotating the shuttle 122 relative to the first and second mixing chambers 106, 108 angularly misaligns the radially-inwardly extending tabs 134 of the shuttle 122 with the radially-outwardly extending tabs 138 of the mixing piston 120 and angularly aligns the channels 136 of the shuttle 122 with the radially-outwardly extending tabs 138 of the mixing piston 120. As a result, the actuator spring 118 is relatively unconstrained and, as shown in FIG. 38, the actuator spring 118 expands and translates the mixing piston 120 into the shuttle 122 and the first mixing chamber 106. The reagents in the first mixing chamber 106 and the second mixing chamber 108 then mix and react to provide a pressurized gas, which the pressure generating actuator 104 delivers from the actuator outlet 114.

Figure 39:
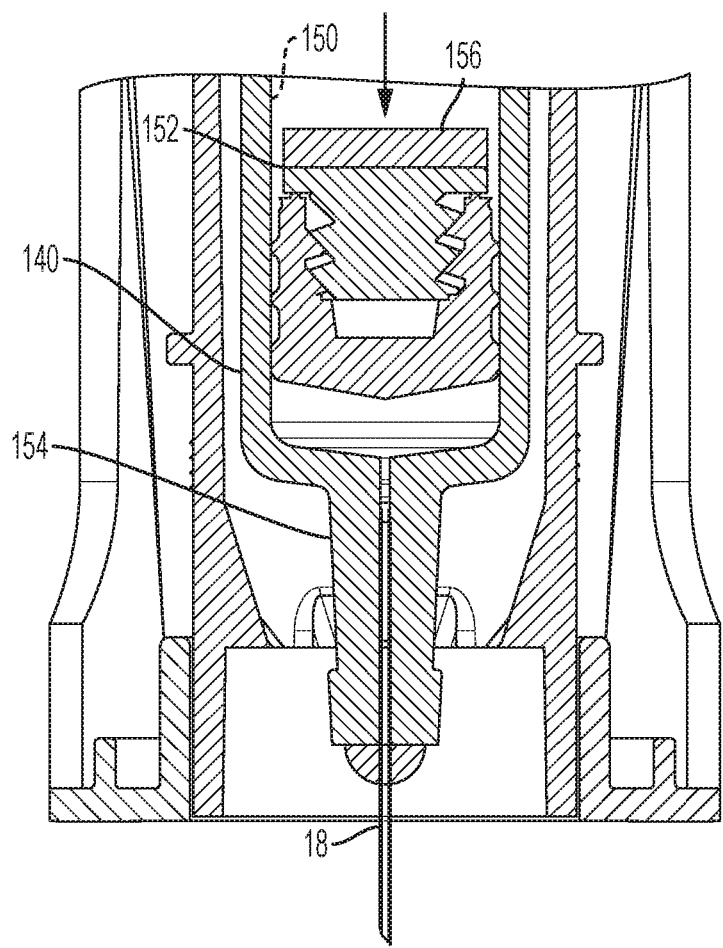
FIG. 39 is a longitudinal sectional partial view of the therapeutic agent delivery system of FIG. 1 upon a syringe piston moving in a syringe passageway to discharge a therapeutic agent from the needle; a syringe chamber is shown in hidden lines to illustrate the syringe piston.

Turning now to FIG. 39, the pressure generating actuator 104 delivers the pressurized gas to the syringe passageway 150, which translates the syringe piston 152 distally within the syringe passageway 150. As such, the syringe piston 152 pushes the therapeutic agent distally to the needle 18, and the needle 18 discharges the therapeutic fluid and delivers the therapeutic fluid to the subject. The piston sensor 172 may sense that the magnetic component 156, and the syringe piston 152, are disposed near the outlet portion 154 of the syringe assembly 140, and the indicator device 168 may provide an indication (for example, visual and/or audible indications).

Figure 41:
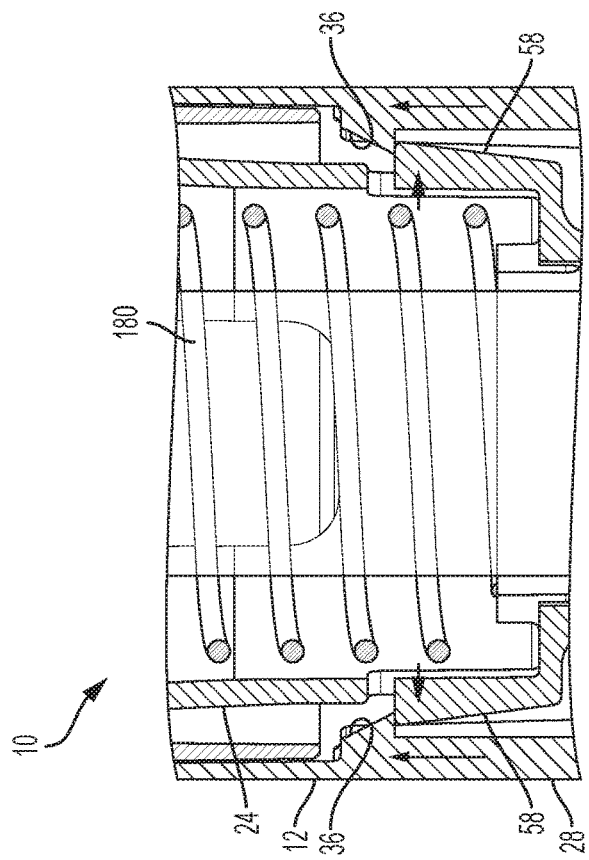
FIG. 41 is a longitudinal sectional view of the therapeutic agent delivery system of FIG. 1 upon tabs of the housing and the sleeve engaging each other; the syringe chamber is shown in hidden lines.
Figure 40:
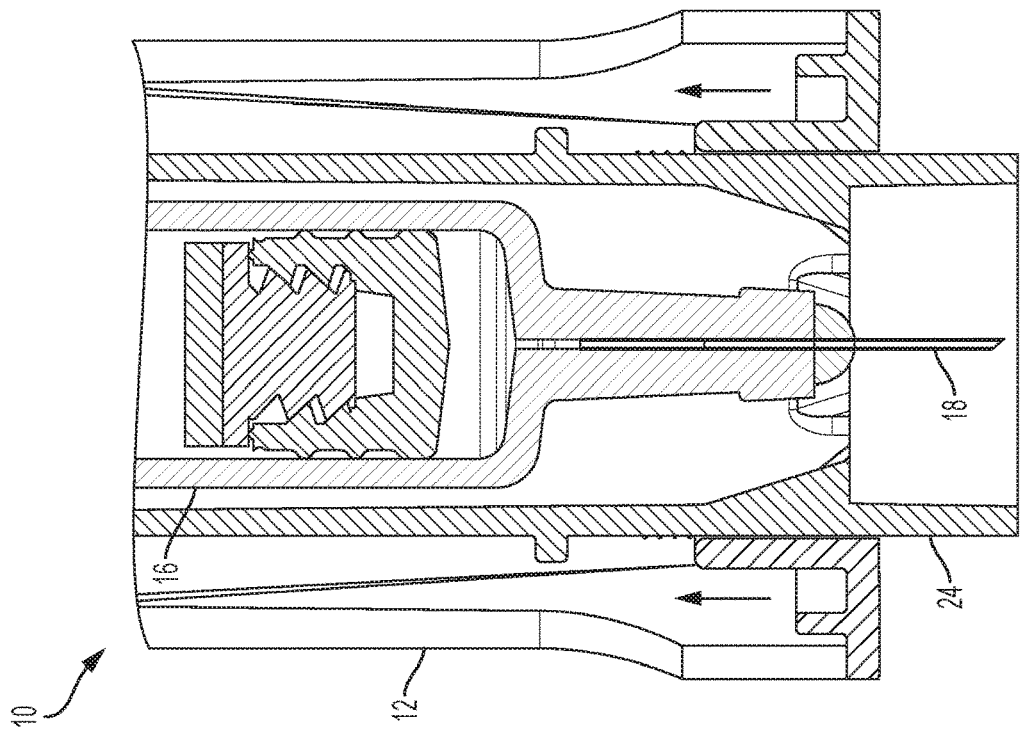
FIG. 40 is a longitudinal sectional partial view of the therapeutic agent delivery system of FIG. 1 upon the syringe passageway and the needle moving to a withdrawn configuration; a syringe chamber is shown in hidden lines to illustrate the syringe piston.
Figure 42:
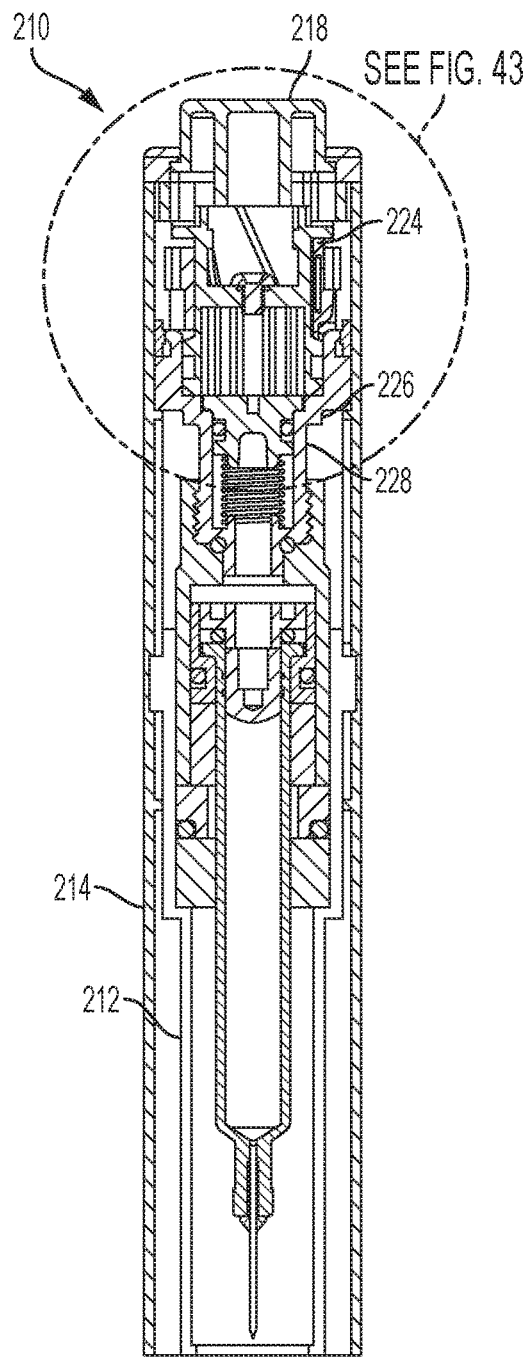
FIG. 42 is longitudinal sectional view of a therapeutic agent delivery system according to another embodiment of the present disclosure.

After the therapeutic agent delivery system 10 discharges the therapeutic agent to the subject and as shown FIGS. 40-41, the user may stop pressing the therapeutic agent delivery system 10 against the surface. As a result, the extension spring 180 is relatively unconstrained and expands to translate the housing 12 and the therapeutic agent delivery assembly 16 proximally relative to the sleeve 24. The needle 18 is thereby disposed in the withdrawn configuration (illustratively, a configuration in which the needle 18 is disposed entirely within the sleeve 24). As shown specifically in FIG. 41, the radially-inwardly extending tabs 36 of the distal housing portion 28 and the radially-outwardly extending tabs 58 of the sleeve 24 engage and slide over each other to inhibit the housing 12 and the therapeutic agent delivery assembly 16 from translating distally relative to the sleeve 24 (that is, the therapeutic agent delivery system 10 may be "locked out"). The therapeutic agent delivery system 10 may then be discarded.

Figure 43:
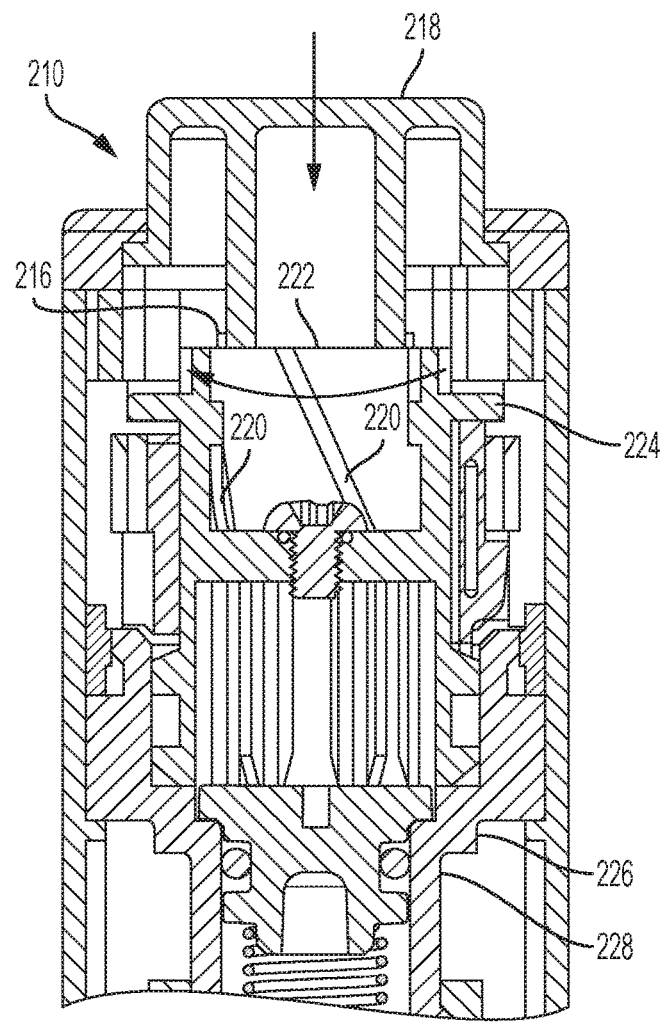
FIG. 43 is a detail longitudinal sectional view of the therapeutic agent delivery system within line 43-43 of FIG. 42.
Figure 44:
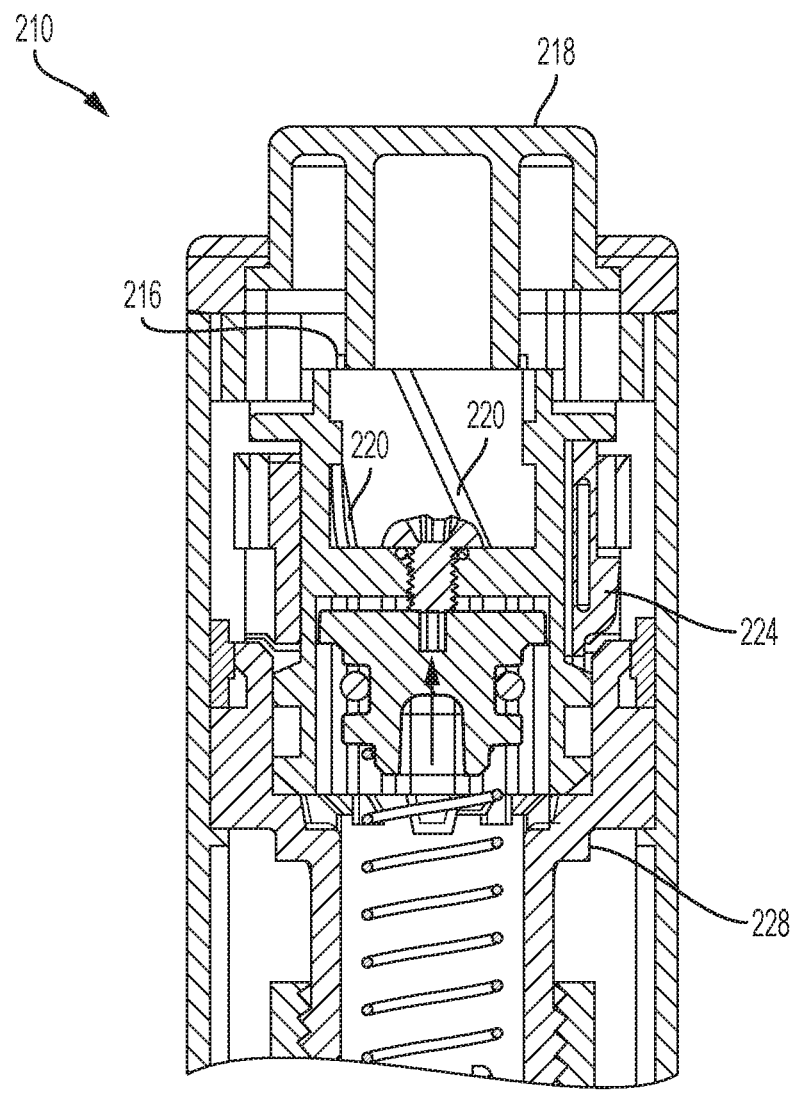
FIG. 44 is a detail longitudinal sectional view of the therapeutic agent delivery system within line 43-43 of FIG. 42 upon a mixing piston of a pressure generating actuator moving to an actuated configuration.
Figure 45:
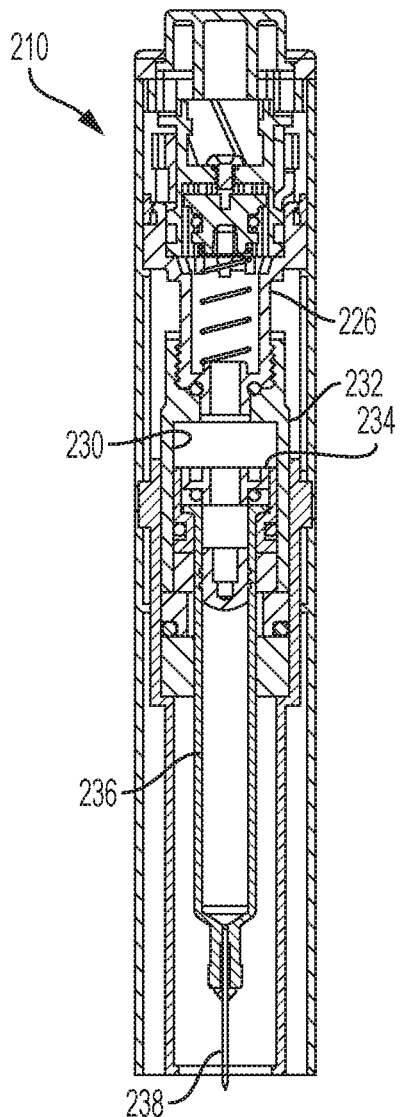
FIG. 45 is longitudinal sectional view of a therapeutic agent delivery system of FIG. 42 upon translation of an intermediate piston and a syringe assembly.
Figure 46:
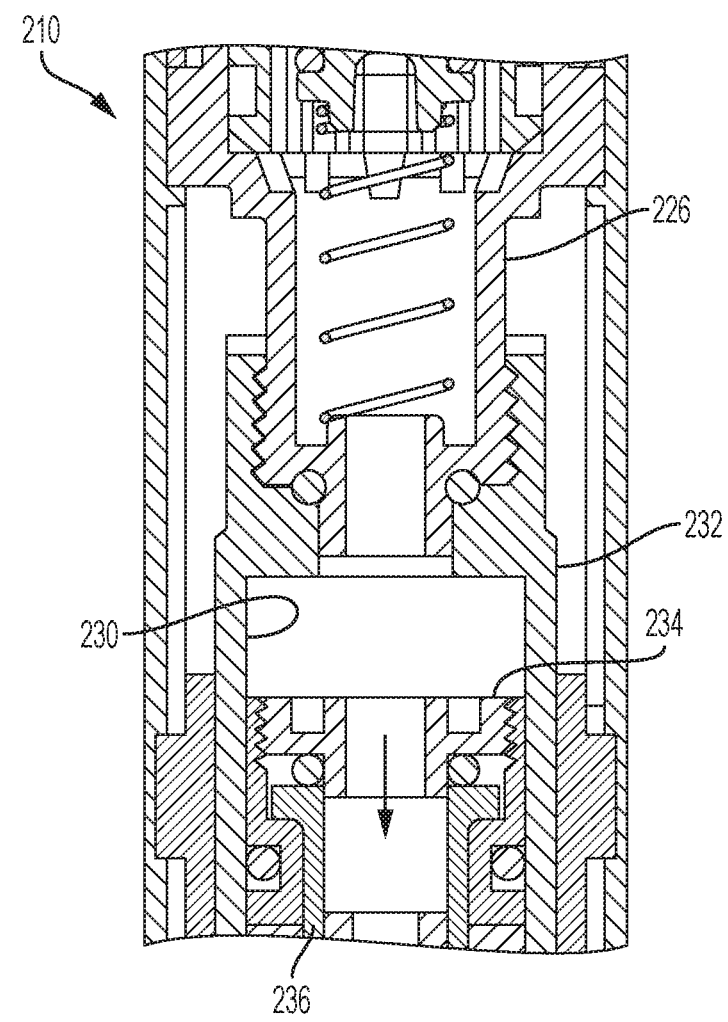
FIG. 46 is a detail longitudinal sectional view of the therapeutic agent delivery system within line 46-46 of FIG. 45.
Figure 47:
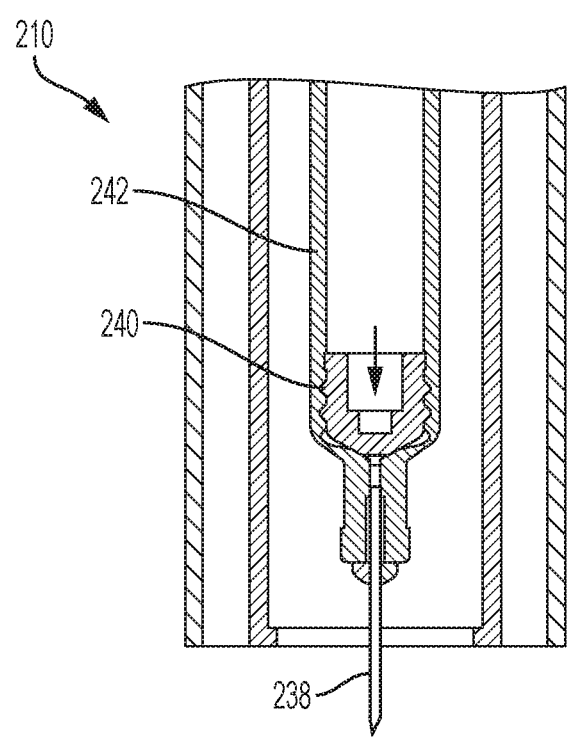
FIG. 47 is a longitudinal sectional partial view of the therapeutic agent delivery system of FIG. 42 upon translation of a syringe piston and delivery of a therapeutic agent.

FIGS. 42-47 illustrate a therapeutic agent delivery system 210 according to another embodiment of the present disclosure. Illustratively, the therapeutic agent delivery system 210 has the same structure as the therapeutic agent delivery system 10, except as described below. The therapeutic agent delivery system 210 is moved from a first configuration to a second configuration (which may also be referred to as an "unlocked" configuration) by pressing a sleeve 212 into a surface (for example, the skin of a subject) and translating the sleeve 212 proximally relative to a housing 214. Then, a user input 218 may be translated distally to actuate the device. More specifically and as shown in FIG. 43, radially-outwardly extending tabs 216 of the user input 218 engage and slide over helically extending ramps 220 formed in a recess 222 of an actuator shuttle 224 of a pressure generating actuator 226. The actuator shuttle 224 thereby rotates relative to an actuator mixing chamber 228 of the pressure generating actuator 226, and the pressure generating actuator 226 is actuated in the same manner as the pressure generating actuator 104 described above. As shown in FIGS. 45-46, the pressure generating actuator 226 delivers pressurized gas to an inner passageway 230 of an actuator coupling 232. The pressurized gas pushes an intermediate piston 234 and a syringe assembly 236 distally, and a needle 238 thereby moves from a stowed configuration to a deployed configuration. As shown in FIG. 47, after the needle 238 reaches the deployed configuration, the pressurized gas pushes a syringe piston 240 distally within a syringe chamber 242. The syringe chamber 242 carries a therapeutic agent opposite the pressure generating actuator 226, and distal movement of the syringe piston 240 causes the syringe chamber 242 to deliver the therapeutic agent to the needle 238, and the needle 238 thereby discharges the therapeutic agent. The needle 238 may then be moved to a withdrawn configuration and the therapeutic agent delivery system 210 may then be locked out in the same manner as the therapeutic agent delivery system 10 described above. The therapeutic agent delivery system 210 may then be discarded.

While the invention has been described as having exemplary designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A therapeutic agent delivery system, comprising:
   a housing having a distal end portion;
   a therapeutic agent delivery assembly carried by the housing, the therapeutic agent delivery assembly comprising:
     a chamber comprising a passageway;
     a therapeutic agent carried in the passageway;
     a needle in communication with the passageway;
     a pressure generating actuator including a mixing chamber and a shuttle carried by the mixing chamber,
   the therapeutic agent delivery assembly being translatable relative to the housing from a stowed configuration to a deployed configuration, in the deployed configuration the needle at least partially extending distally from the distal end portion of the housing;
   a user input configured to be actuated by a user, actuation of the user input translating the therapeutic agent delivery assembly from the stowed configuration to the deployed configuration;
   an input restraint being rotatable relative to the housing from a first rotational configuration to a second rotational configuration, in the first rotational configuration the input restraint inhibiting actuation of the user input, and in the second rotational configuration the input restraint permitting actuation of the user input; and
   a sleeve being translatable relative to the housing from an exposed configuration to a retracted configuration, in the exposed configuration the sleeve at least partially extending distally from the distal end portion of the housing, and the sleeve rotating the input restraint from the first rotational configuration to the second rotational configuration when translating from the exposed configuration to the retracted configuration,
   wherein actuation of the user input causes the pressure generating actuator to pressurize the therapeutic agent, deliver the therapeutic agent from the passageway to the needle, and discharge the therapeutic agent from the needle, wherein pressure generating actuator pressurizes the therapeutic agent upon the shuttle rotating relative to the mixing chamber.

2. The therapeutic agent delivery system of claim 1, further comprising a cam and slot mechanism coupling the input restraint to the sleeve, the cam and slot mechanism causing the input restraint to rotate from the first rotational configuration to the second rotational configuration when the sleeve translates from the exposed configuration to the retracted configuration.

3. The therapeutic agent delivery system of claim 2, wherein the cam and slot mechanism comprises a slot and a cam slidably received in the slot, the sleeve comprises the slot, and the input restraint couples to the cam.

4. The therapeutic agent delivery system of claim 1, wherein the housing defines a longitudinal axis, and the needle translates from the stowed configuration to the deployed configuration in a delivery direction substantially parallel to the longitudinal axis.

5. The therapeutic agent delivery system of claim 4, wherein the input restraint rotates from the first rotational configuration to the second rotational configuration about a rotation axis substantially parallel to the longitudinal axis.

6. The therapeutic agent delivery system of claim 4, wherein the user input is configured to be actuated in an actuation direction substantially parallel to the longitudinal axis.

7. The therapeutic agent delivery system of claim 1, further comprising a spring urging the sleeve toward the exposed configuration.

8. The therapeutic agent delivery system of claim 1, wherein the housing further comprises a proximal end portion opposite the distal end portion, the user input extending proximally from the proximal end portion of the housing.

9. A therapeutic agent delivery system, comprising:
   a housing having a distal end portion;
   a therapeutic agent delivery assembly carried by the housing, the therapeutic agent delivery assembly comprising:
     a chamber comprising a passageway;
     a therapeutic agent carried in the passageway;
     a needle in communication with the passageway;
     a pressure generating actuator in communication with the passageway and comprising a mixing chamber and a shuttle carried by the mixing chamber, actuation of the pressure generating actuator causing delivery of the therapeutic agent from the passageway to the needle and discharge of the therapeutic agent from the needle;
   the therapeutic agent delivery assembly being translatable relative to the housing from a stowed configuration to a deployed configuration, in the deployed configuration the needle at least partially extending distally from the distal end portion of the housing;

a user input configured to be actuated by a user, actuation of the user input actuating the pressure generating actuator, wherein the pressure generating actuator is actuated upon the shuttle rotating relative to the mixing chamber;

an input restraint being rotatable relative to the housing from a first rotational configuration to a second rotational configuration, in the first rotational configuration the input restraint inhibiting actuation of the user input, and in the second rotational configuration the input restraint permitting actuation of the user input; and a sleeve being translatable relative to the housing from an exposed configuration to a retracted configuration, in the exposed configuration the sleeve at least partially extending distally from the distal end portion of the housing, and the sleeve rotating the input restraint from the first rotational configuration to the second rotational configuration when translating from the exposed configuration to the retracted configuration.

10. The therapeutic agent delivery system of claim 9, further comprising a cam and slot mechanism coupling the input restraint to the sleeve, the cam and slot mechanism causing the input restraint to rotate from the first rotational configuration to the second rotational configuration when the sleeve translates from the exposed configuration to the retracted configuration.

11. The therapeutic agent delivery system of claim 9, wherein the housing defines a longitudinal axis, and the therapeutic agent delivery assembly translates from the stowed configuration to the deployed configuration in a delivery direction substantially parallel to the longitudinal axis.

12. A therapeutic agent delivery system, comprising:
a housing having a distal end portion;
a therapeutic agent delivery assembly carried by the housing, the therapeutic agent delivery assembly comprising:
a chamber comprising a passageway;
a therapeutic agent carried in the passageway;
a needle in communication with the passageway;
a pressure generating actuator in communication with the passageway and comprising a mixing chamber and a shuttle carried by the mixing chamber, actuation of the pressure generating actuator causing delivery of the therapeutic agent from the passageway to the needle and discharge of the therapeutic agent from the needle;

the therapeutic agent delivery assembly being translatable relative to the housing from a stowed configuration to a deployed configuration, in the deployed configuration the needle at least partially extending distally from the distal end portion of the housing;

a user input configured to be actuated by a user, actuation of the user input translating the therapeutic agent delivery assembly from the stowed configuration to the deployed configuration and actuating the pressure generating actuator, wherein the pressure generating actuator is actuated upon the shuttle rotating relative to the mixing chamber;

an input restraint being movable relative to the housing from a first configuration to a second configuration, in the first configuration the input restraint inhibiting actuation of the user input, and in the second configuration the input restraint permitting actuation of the user input; and a sleeve being translatable relative to the housing from an exposed configuration to a retracted configuration, in the exposed configuration the sleeve at least partially extending distally from the distal end portion of the housing, and the sleeve moving the input restraint from the first configuration to the second configuration when translating from the exposed configuration to the retracted configuration.

13. The therapeutic agent delivery system of claim 12, wherein the housing defines a longitudinal axis, and the therapeutic agent delivery assembly translates from the stowed configuration to the deployed configuration in a delivery direction substantially parallel to the longitudinal axis.

14. A therapeutic agent delivery system, comprising:
a housing having a proximal end portion and a distal end portion;
a user input coupled to the proximal end portion of the housing and configured to be actuated by a user;
a sleeve coupled to the distal end portion of the housing;
a therapeutic agent delivery assembly carried by the housing, the therapeutic agent delivery assembly comprising:
a chamber comprising a passageway;
a therapeutic agent carried in the passageway;
a needle in communication with the passageway; and
a pressure generating actuator in communication with the passageway, the pressure generating actuator being configured to mix one or more chemical reagents in a mixing chamber in response to an actuation of the user input to generate a pressurized fluid;

the therapeutic agent delivery system having:
a locked configuration in which the sleeve at least partially extends distally from the distal end portion of the housing;
an unlocked configuration in which the sleeve is forced into the distal end portion of the housing;
a deployed configuration in which the needle at least partially extends distally from the distal end portion of the housing, wherein an actuation of the user input causes translation of the therapeutic agent delivery assembly from the unlocked configuration to the deployed configuration;
an actuated configuration in which the pressurized fluid from the pressure generating actuator causes delivery of the therapeutic agent from the passageway to the needle and discharge of the therapeutic agent from the needle.

15. The therapeutic agent delivery system of claim 14, further comprising a rotatable input restraint that inhibits actuation of the user input in the locked configuration and permits actuation of the user input in the unlocked configuration.

16. The therapeutic agent delivery system of claim 14, further comprising:
an extension spring that urges the sleeve into the locked configuration; and
a deployment spring that urges the needle into the deployed configuration.

17. The therapeutic agent delivery system of claim 14, wherein the pressure generating actuator further comprises a shuttle carried by the mixing chamber, wherein the pressure generating actuator pressurizes the therapeutic agent upon the shuttle rotating relative to the mixing chamber.

* * * * *